US00RE50859E

(19) United States
(12) Reissued Patent
Suttin et al.

(10) Patent Number: US RE50,859 E
(45) Date of Reissued Patent: Apr. 14, 2026

(54) TEMPORARY DENTAL PROSTHESIS FOR USE IN DEVELOPING FINAL DENTAL PROSTHESIS

(71) Applicant: Biomet 3i, LLC, Palm Beach Gardens, FL (US)

(72) Inventors: Zachary B. Suttin, Jupiter, FL (US); Stephen M. Herrington, Naples, FL (US); Ross W. Towse, San Marcos, CA (US)

(73) Assignee: Biomet 3i, LLC, Palm Beach Gardens, FL (US)

(21) Appl. No.: 17/974,446

(22) Filed: Oct. 26, 2022

Related U.S. Patent Documents

Reissue of:
(64) Patent No.: 10,813,729
Issued: Oct. 27, 2020
Appl. No.: 13/797,254
Filed: Mar. 12, 2013

U.S. Applications:
(60) Provisional application No. 61/701,416, filed on Sep. 14, 2012.

(51) Int. Cl.
*A61C 13/34* (2006.01)
*A61B 6/03* (2006.01)
(Continued)

(52) U.S. Cl.
CPC ..... *A61C 13/34* (2013.01); *A61B 6/032* (2013.01); *A61B 6/51* (2024.01); *A61C 1/084* (2013.01);
(Continued)

(58) Field of Classification Search
CPC . A61C 13/00; A61C 13/0004; A61C 13/0006; A61C 13/34
See application file for complete search history.

(56) References Cited

U.S. PATENT DOCUMENTS 3,906,634 A 9/1975 Aspel
3,919,772 A 11/1975 Lenczycki
(Continued)

FOREIGN PATENT DOCUMENTS

CN 104955417 A 9/2015
CN 107374762 A 11/2017
(Continued)

OTHER PUBLICATIONS

Biomet 3i—Manual entitled "Navigator™ System for CT Guided Surgery Manual", Revision A Oct. 2007—34 pages.
(Continued)

*Primary Examiner* — Matthew J Kasztejna
(74) *Attorney, Agent, or Firm* — Sheridan Ross P.C.

(57) ABSTRACT

A method of manufacturing a permanent prosthesis for attachment to a dental implant installed in a mouth of a patient includes scanning a patient specific temporary prosthesis (PSTP) to obtain scan data. The PSTP is attached to the dental implant in the mouth of the patient. Gingival tissue surrounding the PSTP is permitted to heal in the mouth of the patient. In response to aesthetics of the healed gingival tissue surrounding the PSTP in the mouth of the patient not being acceptable, the PSTP is physically modified by (i) removing material from the PSTP, (ii) adding material to the PSTP, or (iii) both. The modified PSTP is scanned and a permanent prosthesis is fabricated as a replica of the modified PSTP using scan data generated from the scan of the modified PSTP.

7 Claims, 13 Drawing Sheets

(51) Int. Cl.

| | |
|---|---|
| ***A61B 6/51*** | (2024.01) |
| ***A61C 1/08*** | (2006.01) |
| ***A61C 8/00*** | (2006.01) |
| ***A61C 9/00*** | (2006.01) |
| ***A61C 13/00*** | (2006.01) |
| ***A61C 13/08*** | (2006.01) |

(52) U.S. Cl.
CPC ..... *A61C 8/00* (2013.01); *A61C 9/0053* (2013.01); *A61C 13/00* (2013.01); *A61C 13/08* (2013.01)

(56) References Cited

U.S. PATENT DOCUMENTS 3,958,471 A 5/1976 Muller
4,011,602 A 3/1977 Rybicki et al.
4,056,585 A 11/1977 Waltke
4,086,701 A 5/1978 Kawahara et al.
4,177,562 A 12/1979 Miller et al.
4,294,544 A 10/1981 Altschuler et al.
4,306,862 A 12/1981 Knox
4,325,373 A 4/1982 Slivenko et al.
4,341,312 A 7/1982 Scholer
4,364,381 A 12/1982 Sher et al.
4,439,152 A 3/1984 Small
4,543,953 A 10/1985 Slocum et al.
4,547,157 A 10/1985 Driskell
4,571,180 A 2/1986 Kulick
4,611,288 A 9/1986 Duret et al.
4,624,673 A 11/1986 Meyer
4,663,720 A 5/1987 Duret et al.
4,713,004 A 12/1987 Linkow et al.
4,756,689 A 7/1988 Lundgren
4,758,161 A 7/1988 Niznick
4,767,331 A 8/1988 Hoe
4,772,204 A 9/1988 Soderberg
4,821,200 A 4/1989 Öberg
4,842,518 A 6/1989 Linkow et al.
4,850,870 A 7/1989 Lazzara et al.
4,850,873 A 7/1989 Lazzara et al.
4,854,872 A 8/1989 Detsch
4,856,994 A 8/1989 Lazzara et al.
4,872,839 A 10/1989 Brajnovic
4,906,191 A 3/1990 Soderberg
4,906,420 A 3/1990 Brajnovic
4,931,016 A 6/1990 Sillard
4,935,635 A 6/1990 O'Harra
4,955,811 A * 9/1990 Lazzara et al. ..... 433/173
4,961,674 A 10/1990 Wang et al.
4,964,770 A 10/1990 Steinbichler et al.
4,986,753 A 1/1991 Sellers
4,988,297 A 1/1991 Lazzara et al.
4,988,298 A 1/1991 Lazzara et al.
4,998,881 A 3/1991 Lauks
5,000,685 A 3/1991 Brajnovic
5,006,069 A 4/1991 Lazzara et al.
5,015,183 A 5/1991 Fenick
5,015,186 A 5/1991 Detsch
5,030,096 A 7/1991 Hurson et al.
5,035,619 A 7/1991 Daftary
5,040,982 A 8/1991 Stefan-Dogar
5,040,983 A 8/1991 Binon
5,064,375 A 11/1991 Jörnéus
5,071,351 A 12/1991 Green, Jr. et al.
5,073,111 A 12/1991 Daftary
5,087,200 A 2/1992 Brajnovic et al.
5,100,323 A 3/1992 Friedman et al.
5,104,318 A 4/1992 Piche et al.
5,106,300 A 4/1992 Voitik
5,122,059 A 6/1992 Dürr et al.
5,125,839 A 6/1992 Ingber et al.
5,125,841 A 6/1992 Carlsson et al.
5,133,660 A 7/1992 Fenick
5,135,395 A 8/1992 Marlin
5,145,371 A 9/1992 Jörnëus
5,145,372 A 9/1992 Daftary et al.
5,176,516 A 1/1993 Koizumi
5,188,800 A 2/1993 Green, Jr. et al.
5,195,892 A 3/1993 Gersberg
5,205,745 A 4/1993 Kamiya et al.
5,209,659 A 5/1993 Friedman et al.
5,209,666 A 5/1993 Balfour et al.
5,213,502 A 5/1993 Daftary
5,221,204 A 6/1993 Kruger et al.
5,237,998 A 8/1993 Duret et al.
5,246,370 A 9/1993 Coatoam
5,257,184 A 10/1993 Mushabac
5,281,140 A 1/1994 Niznick
5,286,195 A 2/1994 Clostermann
5,286,196 A 2/1994 Brajnovic et al.
5,292,252 A 3/1994 Nickerson et al.
5,297,963 A 3/1994 Dafatry
5,302,125 A 4/1994 Kownacki et al.
5,312,254 A 5/1994 Rosenlicht
5,312,409 A 5/1994 McLaughlin et al.
5,316,476 A 5/1994 Krauser
5,320,529 A 6/1994 Pompa
5,328,371 A 7/1994 Hund et al.
5,333,898 A 8/1994 Stutz
5,334,024 A 8/1994 Niznick
5,336,090 A 8/1994 Wilson, Jr. et al.
5,338,196 A 8/1994 Beaty et al.
5,338,198 A 8/1994 Wu et al.
5,343,391 A 8/1994 Mushabac
5,344,457 A 9/1994 Pilliar et al.
5,350,297 A 9/1994 Cohen
5,359,511 A 10/1994 Schroeder et al.
5,362,234 A 11/1994 Salazar et al.
5,362,235 A 11/1994 Daftary
5,368,483 A 11/1994 Sutter et al.
5,370,692 A 12/1994 Fink
5,372,502 A 12/1994 Massen et al.
5,386,292 A 1/1995 Massen et al.
5,413,481 A 5/1995 Göppel et al.
5,417,569 A 5/1995 Perisse
5,417,570 A 5/1995 Zuest et al.
5,419,702 A 5/1995 Beaty et al.
5,431,567 A 7/1995 Datary
5,437,551 A 8/1995 Chalifoux
5,440,393 A 8/1995 Wenz
5,452,219 A 9/1995 Dehoff et al.
5,458,488 A 10/1995 Chalifoux
5,476,382 A 12/1995 Daftary
5,476,383 A 12/1995 Beaty et al.
5,492,471 A 2/1996 Singer
5,516,288 A 5/1996 Sichler et al.
5,527,182 A 6/1996 Willoughby
5,533,898 A 7/1996 Mena
5,538,426 A 7/1996 Harding et al.
5,547,377 A 8/1996 Daftary
5,556,278 A 9/1996 Meitner
5,561,675 A 10/1996 Bayon et al.
5,564,921 A 10/1996 Marlin
5,564,924 A 10/1996 Kwan
5,569,578 A 10/1996 Mushabac
5,575,656 A 11/1996 Hajjar
5,580,244 A 12/1996 White
5,580,246 A 12/1996 Fried
5,595,703 A 1/1997 Swaelens et al.
5,613,832 A 3/1997 Su
5,613,852 A 3/1997 Bavitz
5,630,717 A 5/1997 Zuest
5,636,986 A 6/1997 Pezeshkian
5,651,675 A 7/1997 Singer
5,652,709 A 7/1997 Andersson et al.
5,658,147 A 8/1997 Phimmasone
5,662,476 A 9/1997 Ingber et al.
5,674,069 A 10/1997 Osorio
5,674,071 A 10/1997 Beaty et al.
5,674,073 A 10/1997 Ingber et al.
5,681,167 A 10/1997 Lazarof
5,685,715 A 11/1997 Beaty et al.
5,688,283 A 11/1997 Knapp
5,704,936 A 1/1998 Mazel

(56) References Cited

U.S. PATENT DOCUMENTS 5,718,579 A 2/1998 Kennedy
5,725,376 A 3/1998 Poirier
5,733,124 A 3/1998 Kwan
5,741,215 A 4/1998 Fink
5,743,916 A 4/1998 Greenberg
5,759,036 A 6/1998 Hinds
5,762,125 A 6/1998 Mastrorio
5,762,500 A 6/1998 Lazarof
5,768,134 A 6/1998 Swaelens et al.
5,769,636 A 6/1998 Di Sario
5,791,902 A 8/1998 Lauks
5,800,168 A 9/1998 Cascione et al.
5,813,858 A 9/1998 Singer
5,823,778 A 10/1998 Schmitt et al.
5,842,859 A 12/1998 Palacci
5,846,079 A 12/1998 Knode
5,851,115 A 12/1998 Carlsson et al.
5,857,853 A 1/1999 Van Nifterick et al.
5,871,358 A 2/1999 Ingber et al.
5,873,722 A 2/1999 Lazzara et al.
5,876,204 A 3/1999 Day et al.
5,885,078 A 3/1999 Cagna et al.
5,888,034 A 3/1999 Greenberg
5,904,483 A 5/1999 Wade
5,915,962 A 6/1999 Rosenlicht
5,927,982 A 7/1999 Kruger
5,938,443 A 8/1999 Lazzara et al.
5,954,769 A 9/1999 Rosenlicht
5,964,591 A 10/1999 Beaty et al.
5,967,777 A 10/1999 Klein et al.
5,984,681 A 11/1999 Huang
5,989,025 A 11/1999 Conley
5,989,029 A 11/1999 Osorlo
5,989,258 A 11/1999 Hattori
5,997,681 A 12/1999 Kinzie
6,000,939 A 12/1999 Ray et al.
6,008,905 A 12/1999 Breton et al.
6,068,479 A 5/2000 Kwan
6,099,311 A 8/2000 Wagner et al.
6,099,313 A 8/2000 Dorken et al.
6,099,314 A 8/2000 Kopelman et al.
6,120,293 A 9/2000 Lazzara et al.
6,129,548 A 10/2000 Lazzara et al.
6,135,773 A 10/2000 Lazzara
6,142,782 A 11/2000 Lazarof
6,174,168 B1 1/2001 Dehoff et al.
6,175,413 B1 1/2001 Lucas
6,190,169 B1 2/2001 Bluemli et al.
6,197,410 B1 3/2001 Vallittu et al.
6,200,125 B1 3/2001 Akutagawa
6,206,693 B1 3/2001 Hultgren
6,210,162 B1 4/2001 Chishti
6,217,334 B1 4/2001 Hultgren
6,227,859 B1 5/2001 Sutter
6,283,753 B1 9/2001 Willoughby
6,287,119 B1 9/2001 van Nifterick
6,296,483 B1 10/2001 Champleboux
6,305,939 B1 10/2001 Dawood
6,319,000 B1 11/2001 Branemark
6,322,728 B1 11/2001 Brodkin
6,382,975 B1 5/2002 Poirier
6,402,707 B1 6/2002 Ernst
6,431,866 B2 8/2002 Hurson
6,431,867 B1 8/2002 Gittelson et al.
6,488,503 B1 12/2002 Lichkus et al.
6,497,574 B1 12/2002 Miller
6,540,784 B2 4/2003 Barlow
6,558,162 B1 5/2003 Porter et al.
6,568,936 B2 5/2003 MacDougald
6,575,751 B1 6/2003 Lehmann et al.
6,594,539 B1 7/2003 Geng
6,610,079 B1 8/2003 Li
6,619,958 B2 9/2003 Beaty et al.
6,629,840 B2 10/2003 Chishti
6,634,883 B2 10/2003 Ranalli
6,644,970 B1 11/2003 Lin
6,648,640 B2 11/2003 Rubbert et al.
6,671,539 B2 12/2003 Gateno et al.
6,672,870 B2 1/2004 Knapp
6,688,887 B2 2/2004 Morgan
6,691,764 B2 2/2004 Embert
6,743,491 B2 6/2004 Cirincione et al.
6,755,652 B2 6/2004 Nanni
6,772,026 B2 8/2004 Bradbury
6,776,614 B2 8/2004 Wiechmann et al.
6,783,359 B2 8/2004 Kapit
6,790,040 B2 9/2004 Amber et al.
6,793,491 B2 9/2004 Klein et al.
6,808,659 B2 10/2004 Schulman
6,814,575 B2 11/2004 Poirier
6,821,462 B2 11/2004 Schulamn et al.
6,829,498 B2 12/2004 Kipke et al.
D503,804 S 4/2005 Phleps et al.
6,882,894 B2 4/2005 Durbin et al.
6,885,464 B1 4/2005 Pfeiffer et al.
6,902,401 B2 6/2005 Jorneus et al.
6,913,463 B2 7/2005 Blacklock
6,926,442 B2 8/2005 Stöckl
6,926,525 B1 8/2005 Ronvig
6,939,489 B2 9/2005 Moszner et al.
6,942,699 B2 9/2005 Stone et al.
6,953,383 B2 10/2005 Rothenberger
6,957,118 B2 10/2005 Kopelman et al.
6,966,772 B2 11/2005 Malin et al.
6,970,760 B2 11/2005 Wolf et al.
6,971,877 B2 12/2005 Harter
6,994,549 B2 2/2006 Brodkin et al.
7,010,150 B1 3/2006 Pfeiffer et al.
7,010,153 B2 3/2006 Zimmermann
7,012,988 B2 3/2006 Adler et al.
7,018,207 B2 3/2006 Prestipino
7,021,934 B2 4/2006 Aravena
7,029,275 B2 4/2006 Rubbert et al.
7,044,735 B2 5/2006 Malin
7,056,115 B2 6/2006 Phan et al.
7,056,472 B1 6/2006 Behringer
7,059,856 B2 6/2006 Marotta
7,066,736 B2 6/2006 Kumar et al.
7,084,868 B2 8/2006 Farag et al.
7,086,860 B2 8/2006 Schuman et al.
7,097,451 B2 8/2006 Tang
7,104,795 B2 9/2006 Dadi
7,110,844 B2 9/2006 Kopelman
7,112,065 B2 9/2006 Kopelman
7,118,375 B2 10/2006 Durbin et al.
D532,991 S 12/2006 Gozzi
7,153,132 B2 12/2006 Tedesco
7,153,135 B1 12/2006 Thomas
7,163,443 B2 1/2007 Basler et al.
7,175,434 B2 2/2007 Brajnovic
7,175,435 B2 2/2007 Andersson et al.
7,178,731 B2 2/2007 Basler
7,214,062 B2 5/2007 Morgan
7,220,124 B2 5/2007 Taub et al.
7,228,191 B2 6/2007 Hofmeister et al.
7,236,842 B2 6/2007 Kopelman et al.
7,281,927 B2 10/2007 Marotta
7,286,954 B2 10/2007 Kopelman et al.
7,303,420 B2 12/2007 Huch et al.
7,319,529 B2 1/2008 Babayoff
7,322,746 B2 1/2008 Beckhaus et al.
7,322,824 B2 1/2008 Schmitt
7,324,680 B2 1/2008 Zimmermann
7,329,122 B1 2/2008 Scott
7,333,874 B2 2/2008 Taub et al.
7,335,876 B2 2/2008 Eiff et al.
D565,184 S 3/2008 Royzen
7,367,801 B2 5/2008 Saliger
7,379,584 B2 5/2008 Rubbert et al.
D571,471 S 6/2008 Stöckl
7,381,191 B2 6/2008 Fallah
7,383,094 B2 6/2008 Kopelman et al.
D575,747 S 8/2008 Abramovich et al.
7,421,608 B2 9/2008 Schron

(56) References Cited

U.S. PATENT DOCUMENTS 7,425,131 B2 9/2008 Amber et al.
7,429,175 B2 9/2008 Gittelson
7,435,088 B2 10/2008 Brajnovic
7,476,100 B2 1/2009 Kuo
7,481,647 B2 1/2009 Sambu et al.
7,488,174 B2 2/2009 Kopelman et al.
7,497,619 B2 3/2009 Stoeckl
7,497,983 B2 3/2009 Khan et al.
7,520,747 B2 4/2009 Stonisch
7,522,764 B2 4/2009 Schwotzer
7,534,266 B2 5/2009 Kluger
7,536,234 B2 5/2009 Kopelman et al.
7,545,372 B2 6/2009 Kopelman et al.
7,551,760 B2 6/2009 Scharlack et al.
7,555,403 B2 6/2009 Kopelman et al.
7,556,496 B2 7/2009 Cinader, Jr. et al.
7,559,692 B2 7/2009 Beckhaus et al.
7,563,397 B2 7/2009 Schulman et al.
D597,769 S 8/2009 Richter et al.
7,572,058 B2 8/2009 Pruss et al.
7,572,125 B2 8/2009 Brajnovic
7,574,025 B2 8/2009 Feldman
7,578,673 B2 8/2009 Wen et al.
7,580,502 B2 8/2009 Dalpiaz et al.
7,581,951 B2 9/2009 Lehmann et al.
7,582,855 B2 9/2009 Pfeiffer
7,628,537 B2 12/2009 Schulze-Ganzlin
7,632,097 B2 12/2009 Clerck
7,653,455 B2 1/2010 Cnader, Jr. et al.
7,654,823 B2 2/2010 Dadi
7,655,586 B1 2/2010 Brodkin et al.
7,658,610 B2 2/2010 Knopp
7,661,956 B2 2/2010 Powell et al.
7,665,989 B2 2/2010 Brajnovic et al.
7,679,723 B2 3/2010 Schwotzer
7,687,754 B2 3/2010 Eiff et al.
7,689,308 B2 3/2010 Holzner et al.
D614,210 S 4/2010 Basler et al.
7,698,014 B2 4/2010 Dunne et al.
7,758,346 B1 7/2010 Letcher
7,774,084 B2 8/2010 Cinader, Jr.
7,780,907 B2 8/2010 Schmidt et al.
7,785,007 B2 8/2010 Stoeckl
7,787,132 B2 8/2010 Körner et al.
7,796,811 B2 9/2010 Orth et al.
7,798,708 B2 9/2010 Erhardt et al.
7,801,632 B2 9/2010 Orth et al.
7,815,371 B2 10/2010 Schulze-Ganzlin
7,824,181 B2 11/2010 Sers
D629,908 S 12/2010 Jerger et al.
7,855,354 B2 12/2010 Eiff
7,865,261 B2 * 1/2011 Pfeiffer ..... 700/118
7,876,877 B2 1/2011 Stockl
7,901,209 B2 3/2011 Saliger et al.
7,982,731 B2 7/2011 Orth et al.
7,985,119 B2 7/2011 Basler et al.
7,986,415 B2 7/2011 Thiel et al.
7,988,449 B2 8/2011 Amber et al.
8,011,925 B2 9/2011 Powell et al.
8,011,927 B2 9/2011 Merckmans, III et al.
8,026,943 B2 9/2011 Weber et al.
8,038,440 B2 10/2011 Swaelens et al.
8,047,895 B2 11/2011 Basler
8,057,912 B2 11/2011 Basler et al.
8,062,034 B2 11/2011 Hanisch et al.
8,075,313 B2 12/2011 Ranck et al.
8,083,522 B2 12/2011 Karkar et al.
8,105,081 B2 1/2012 Bavar
8,226,654 B2 7/2012 Ranck et al.
8,454,365 B2 6/2013 Boerjes et al.
2001/0008751 A1 7/2001 Chishti et al.
2001/0034010 A1 10/2001 MacDougald et al.
2002/0010568 A1 1/2002 Rubbert et al.
2002/0028418 A1 3/2002 Farag et al.
2002/0039717 A1 4/2002 Amber et al.
2002/0150859 A1 10/2002 Imgrund et al.
2002/0160337 A1 10/2002 Klein et al.
2002/0167100 A1 11/2002 Moszner
2003/0130605 A1 7/2003 Besek
2003/0222366 A1 12/2003 Stangel
2004/0029074 A1 2/2004 Brajnovic
2004/0048227 A1 3/2004 Brajnovic
2004/0180308 A1 9/2004 Ebi et al.
2004/0219477 A1 11/2004 Harter
2004/0219479 A1 11/2004 Malin et al.
2004/0219490 A1 11/2004 Gartner et al.
2004/0220691 A1 11/2004 Hofmeister et al.
2004/0241611 A1 12/2004 Amber et al.
2004/0243481 A1 12/2004 Bradbury et al.
2004/0259051 A1 12/2004 Brajnovic
2005/0023710 A1 2/2005 Brodkin et al.
2005/0056350 A1 3/2005 Dolabdjian et al.
2005/0070782 A1 3/2005 Brodkin
2005/0084144 A1 4/2005 Feldman
2005/0100861 A1 5/2005 Choi et al.
2005/0170311 A1 8/2005 Tardieu et al.
2005/0271996 A1 12/2005 Sporbert et al.
2005/0277089 A1 12/2005 Brajnovic
2005/0277090 A1 12/2005 Anderson et al.
2005/0277091 A1 12/2005 Andersson et al.
2005/0282106 A1 12/2005 Sussman et al.
2005/0283065 A1 12/2005 Babayoff
2006/0006561 A1 1/2006 Brajnovic
2006/0008763 A1 1/2006 Brajnovic
2006/0008770 A1 1/2006 Brajnovic et al.
2006/0093988 A1 5/2006 Swaelens et al.
2006/0094951 A1 5/2006 Dean et al.
2006/0127848 A1 6/2006 Sogo et al.
2006/0210949 A1 9/2006 Stoop
2006/0263741 A1 11/2006 Imgrund et al.
2006/0281041 A1 12/2006 Rubbert et al.
2007/0015111 A1 1/2007 Kopelman et al.
2007/0031790 A1 2/2007 Raby et al.
2007/0065777 A1 3/2007 Becker
2007/0077532 A1 4/2007 Harter
2007/0092854 A1 4/2007 Powell et al.
2007/0141525 A1 6/2007 Cinader, Jr.
2007/0154866 A1 * 7/2007 Hall ..... A61C 13/0004 433/213
2007/0211081 A1 9/2007 Quadling et al.
2007/0218426 A1 9/2007 Quadling et al.
2007/0269769 A1 11/2007 Marchesi
2007/0281277 A1 12/2007 Brajnovic
2008/0015727 A1 * 1/2008 Dunne ..... A61B 5/4547 700/118
2008/0038692 A1 2/2008 Andersson et al.
2008/0044794 A1 2/2008 Brajnovic
2008/0057467 A1 3/2008 Gittelson
2008/0070181 A1 3/2008 Abolfathi et al.
2008/0085489 A1 4/2008 Schmitt
2008/0090210 A1 4/2008 Brajnovic
2008/0114371 A1 5/2008 Kluger
2008/0118895 A1 5/2008 Brajnovic
2008/0124676 A1 5/2008 Marotta
2008/0153060 A1 6/2008 De Moyer
2008/0153061 A1 6/2008 Marcello
2008/0153065 A1 6/2008 Brajnovic et al.
2008/0153069 A1 6/2008 Holzner et al.
2008/0176189 A1 7/2008 Stonisch
2008/0206714 A1 * 8/2008 Schmitt ..... 433/215
2008/0233537 A1 9/2008 Amber et al.
2008/0233539 A1 9/2008 Rossler et al.
2008/0241798 A1 10/2008 Holzner et al.
2008/0261165 A1 10/2008 Steingart et al.
2008/0261176 A1 10/2008 Hurson
2008/0286722 A1 11/2008 Berckmans, III et al.
2008/0300716 A1 12/2008 Kopelman et al.
2009/0017418 A1 1/2009 Gittelson
2009/0026643 A1 1/2009 Wiest et al.
2009/0042167 A1 2/2009 Van Der Zel
2009/0081616 A1 3/2009 Pfeiffer
2009/0087817 A1 4/2009 Jansen et al.
2009/0092948 A1 4/2009 Gantes
2009/0098510 A1 4/2009 Zhang

(56) References Cited

U.S. PATENT DOCUMENTS

| | | | | |
|---|---|---|---|---|
| 2009/0098511 | A1 | 4/2009 | Zhang | |
| 2009/0123045 | A1 | 5/2009 | Quadling et al. | |
| 2009/0123887 | A1 | 5/2009 | Brajnovic | |
| 2009/0130630 | A1 | 5/2009 | Suttin et al. | |
| 2009/0186319 | A1 | 7/2009 | Sager | |
| 2009/0187393 | A1 | 7/2009 | Van Lierde et al. | |
| 2009/0220134 | A1 | 9/2009 | Cahill et al. | |
| 2009/0220916 | A1 | 9/2009 | Fisker et al. | |
| 2009/0220917 | A1 | 9/2009 | Jensen | |
| 2009/0239197 | A1 | 9/2009 | Brajnovic | |
| 2009/0239200 | A1 | 9/2009 | Brajnovic et al. | |
| 2009/0253097 | A1 | 10/2009 | Brajnovic | |
| 2009/0263764 | A1 | 10/2009 | Berckmans, III et al. | |
| 2009/0287332 | A1 | 11/2009 | Adusumilli et al. | |
| 2009/0298009 | A1 | 12/2009 | Brajnovic | |
| 2009/0298017 | A1 | 12/2009 | Boerjes et al. | |
| 2009/0317763 | A1 | 12/2009 | Brajnovic | |
| 2009/0325122 | A1 | 12/2009 | Brajnovic et al. | |
| 2010/0009314 | A1 | 1/2010 | Tardieu et al. | |
| 2010/0028827 | A1 | 2/2010 | Andersson et al. | |
| 2010/0038807 | A1 | 2/2010 | Brodkin et al. | |
| 2010/0075275 | A1 | 3/2010 | Brajnovic | |
| 2010/0092904 | A1 | 4/2010 | Esposti et al. | |
| 2010/0105008 | A1 | 4/2010 | Powell et al. | |
| 2010/0105009 | A1 | 4/2010 | Karkar et al. | |
| 2010/0151420 | A1 | 6/2010 | Ranck | |
| 2010/0151423 | A1 | 6/2010 | Ranck et al. | |
| 2010/0173260 | A1 | 7/2010 | Sogo et al. | |
| 2010/0209877 | A1 | 8/2010 | Hogan et al. | |
| 2010/0280798 | A1 | 11/2010 | Pattijn et al. | |
| 2011/0008751 | A1 | 1/2011 | Pettersson | |
| 2011/0060558 | A1 | 3/2011 | Pettersson | |
| 2011/0129792 | A1 | 6/2011 | Berckmans, III et al. | |
| 2011/0183289 | A1* | 7/2011 | Powell et al. | 433/173 |
| 2011/0183290 | A1* | 7/2011 | Galgut et al. | 433/174 |
| 2011/0191081 | A1 | 8/2011 | Malfliet et al. | |
| 2011/0244426 | A1 | 10/2011 | Amber et al. | |
| 2011/0269104 | A1 | 11/2011 | Berckmans, III et al. | |
| 2011/0275032 | A1 | 11/2011 | Tardieu et al. | |
| 2011/0306008 | A1 | 12/2011 | Suttin et al. | |
| 2011/0306009 | A1 | 12/2011 | Suttin et al. | |
| 2011/0306014 | A1 | 12/2011 | Conte et al. | |
| 2012/0010740 | A1 | 1/2012 | Swaelens et al. | |
| 2012/0115105 | A1* | 5/2012 | Schneider | 433/173 |
| 2012/0135370 | A1 | 5/2012 | Ranck et al. | |
| 2012/0164593 | A1 | 6/2012 | Bavar | |
| 2012/0164893 | A1 | 6/2012 | Mitsuzuka et al. | |
| 2012/0189982 | A1 | 7/2012 | Powell et al. | |
| 2012/0214130 | A1 | 8/2012 | Krivoruk | |
| 2012/0330315 | A1 | 12/2012 | Ranck et al. | |
| 2013/0177872 | A1* | 7/2013 | Blaisdell et al. | 433/173 |
| 2014/0080092 | A1 | 3/2014 | Suttin et al. | |

FOREIGN PATENT DOCUMENTS

| | | | |
|---|---|---|---|
| DE | 10029256 | | 11/2000 |
| JP | 2005168518 | A | 6/2005 |
| JP | 2009501036 | A | 1/2009 |
| JP | 2012521236 | A | 9/2012 |
| JP | 2015531652 | A | 11/2015 |
| WO | WO 1994/26200 | | 11/1994 |
| WO | WO 1999/032045 | | 7/1999 |
| WO | WO 2000/008415 | | 2/2000 |
| WO | WO 2001/058379 | | 8/2001 |
| WO | WO 2002/053055 | | 7/2002 |
| WO | WO 2003/024352 | | 3/2003 |
| WO | WO 2004/030565 | | 4/2004 |
| WO | WO 2004/075771 | | 9/2004 |
| WO | WO 2004/087000 | | 10/2004 |
| WO | WO 2004/098435 | | 11/2004 |
| WO | WO 2006/014130 | | 2/2006 |
| WO | WO 2006/062459 | | 6/2006 |
| WO | WO 2006/082198 | | 8/2006 |
| WO | WO 2007/005490 | | 1/2007 |
| WO | WO 2007/033157 | | 3/2007 |
| WO | WO 2007/104842 | | 9/2007 |
| WO | WO 2007/129955 | | 11/2007 |
| WO | WO 2008/057955 | | 5/2008 |
| WO | WO 2008/083857 | | 7/2008 |
| WO | WO 2009/146164 | | 12/2009 |
| WO | WO 2010108935 | * | 9/2010 |
| WO | 2012113407 | | 8/2012 |

OTHER PUBLICATIONS

Francois Goulette, "A New Method and a Clinical case for Computer Assisted Dental Implantology." Retrieved from Summer European university in surgical Robotics, URL:www.lirmm.fr/manifs/UEE/docs/students/goulette.pdf Sep. 6, 2003 (7 pages).

International Search Report for International Application No. PCT/US2009/034463, filed Feb. 19, 2009, dated Apr. 30, 2009 (2 pages).

Jakob Brief, "Accuracy of image-guided implantology." Retrieved from Google, <URL:sitemaker.umich,edu/sarmentlab/files/robodent_vs_denx_coir_05.pdf, Aug. 20, 2004 (7 pages).

Machine Design: "Robots are ready for medical manufacturing." Retrieved from MachineDesign.Com, <URL: http://machinedesign.com/article/robots-are-ready-for-medical-manufacturing-0712>, Jul. 12, 2007 (7 pages).

MedNEWS: "'Surgical Glue' May Help to Eliminate Suturing for Implants." Retrieved from MediNEWS.Direct, URL:http://www.medinewsdirect.com/?p=377, Dec. 21, 2007 (1 page).

Written Opinion of International Application No. PCT/US2009/034463, filed Feb. 19, 2009, dated Apr. 30, 2009 (6 pages).

International Search Report for International Application No. PCT/US2012/038097, filed May 16, 2012, dated Sep. 7, 2012 (2 pages).

International Written Opinion for International Application No. PCT/US2012/038097, filed May 16, 2012, dated Sep. 7, 2012 (9 pages).

"U.S. Appl. No. 13/797,385, Response filed Dec. 16, 2016 to Advisory Action dated Dec. 9, 2016", 13 pgs.

"Chinese Application Serial No. 201380059563.1, Office Action dated Jan. 17, 2017", W/ English Translation, 7 pgs.

"Chinese Application Serial No. 201380059563.1, Response Filed Mar. 31, 2017 to Office Action dated Jan. 17, 2017", (W/ English Translation), 12 pgs.

"Japanese Application Serial No. 2015-531988, Office Action dated May 16, 2017", (W/ English Translation), 13 pgs.

Edmond, H Pow, et al., "A Modified Implant Healing Abutment to Optimize Soft Tissue Contours: A Case Report, Implant dentistry", vol. 13, No. 4, (2004), 297-299.

"U.S. Appl. No. 13/797,385, Advisory Action dated Dec. 9, 2016", 3 pgs.

"U.S. Appl. No. 13/797,385, Response filed Nov. 7, 2016 to Final Office Action dated Jul. 7, 2016", 13 pgs.

"Japanese Application Serial No. 2015-531988, Response filed Nov. 30, 2016 to Office Action dated Aug. 30, 2016", W/ English Translation of Claims, 12 pgs.

"U.S. Appl. No. 13/797,385, Non Final Office Action dated Nov. 20, 2017", 12 pgs.

"U.S. Appl. No. 13/797,385, Response filed Feb. 20, 2018 to Non Final Office Action dated Nov. 20, 2017", 13 pgs.

"Australian Application Serial No. 2013315768, First Examination Report dated Sep. 14, 2017", 6 pgs.

"U.S. Appl. No. 13/797,385, Examiner Interview Summary dated Apr. 30, 2018", 2 pgs.

"U.S. Appl. No. 13/797,385, Final Office Action dated May 10, 2018", 12 pgs.

"U.S. Appl. No. 13/797,385, Response filed Oct. 10, 2018 to Final Office action dated May 10, 2018", 15 pgs.

"Australian Application Serial No. 2013315768, Response filed Sep. 7, 2018 to Subsequent Examiners Report dated Sep. 3, 2018", 19 pgs.

"Australian Application Serial No. 2013315768, Subsequent Examiners Report dated Sep. 3, 2018", 4 pgs.

"Japanese Application Serial No. 2015-531988, Examiners Decision of Final Refusal dated Feb. 6, 2018", (W/ English Translation), 9 pgs.

(56) References Cited

OTHER PUBLICATIONS

"U.S. Appl. No. 13/797,385, Non Final Office Action dated Feb. 27, 2019", 14 pgs.
"U.S. Appl. No. 13/797,385, Response filed Aug. 26, 2019 to Non Final Office Action dated Feb. 27, 2019", 14 pgs.
"Canadian Application Serial No. 2,884,009, Examiner's Rule 30(2) Requisition dated Jul. 11, 2019", 4 pgs.
"Chinese Application Serial No. 201710531878.1, Office Action dated Jul. 29, 2019", with English translation, 14 pages.
"Japanese Application Serial No. 2015-531988, Office Action dated Aug. 30, 2016", w/ English Translation, 14 pgs.
"Israel Application Serial No. 237609, Response filed Nov. 4, 2019 to Office Action dated Jul. 9, 2019", 3 pages.
"U.S. Appl. No. 13/797,385, Examiner Interview Summary dated Apr. 19, 2016", 3 pgs.
"U.S. Appl. No. 13/797,385, Examiner Interview Summary dated May 13, 2015", 4 pgs.
"U.S. Appl. No. 13/797,385, Final Office Action dated Feb. 3, 2015", 16 pgs.
"U.S. Appl. No. 13/797,385, Non Final Office Action dated Aug. 6, 2014", 18 pgs.
"U.S. Appl. No. 13/797,385, Non Final Office Action dated Nov. 17, 2015", 16 pgs.
"U.S. Appl. No. 13/797,385, Preliminary Amendment filed Mar. 12, 2013", 6 pgs.
"U.S. Appl. No. 13/797,385, Response filed Apr. 18, 2016 to Non Final Office Action dated Nov. 17, 2015", 14 pgs.
"U.S. Appl. No. 13/797,385, Response filed May 7, 2015 to Final Office Action dated Feb. 3, 2015", 12 pgs.
"U.S. Appl. No. 13/797,385, Response filed Jun. 18, 2014 to Restriction Requirement dated Apr. 30, 2014", 6 pgs.
"U.S. Appl. No. 13/797,385, Response filed Dec. 2, 2014 to Non Final Office Action dated Aug. 6, 2014", 15 pgs.
"U.S. Appl. No. 13/797,385, Restriction Requirement dated Apr. 30, 2014", 6 pgs.
"European Application Serial No. 13762714.7, Response filed Aug. 20, 2015 to Communication pursuant to Rules 161(1) and 162 EPC dated May 6, 2015", 8 pgs.
"International Application Serial No. PCT/US2013/058802, International Preliminary Report on Patentability dated Aug. 8, 2014", 12 pgs.
"International Application Serial No. PCT/US2013/058802, International Search Report dated Jan. 23, 14", 2 pgs.
"International Application Serial No. PCT/US2013/058802, Written Opinion dated Jan. 23, 2014", 4 pgs.
"Australian Application Serial No. 2019200020, First Examination Report dated Feb. 19, 2020", 6 pages.
"Canadian Application Serial No. 2,884,009, Office Action dated Jun. 2, 2020", 4 pages.

* cited by examiner

TEMPORARY DENTAL PROSTHESIS FOR USE IN DEVELOPING FINAL DENTAL PROSTHESIS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATION

This application *is a Broadening Reissue of U.S. patent application Ser. No. 13/797,254, filed Mar. 12, 2013, now U.S. Pat. No. 10,813,729; which* claims the benefit of U.S. Provisional Application No. 61/701,416, filed Sep. 14, 2012; this application is related to U.S. Application Ser. No. 13/797,385, filed Mar. 12, 2013, entitled "Temporary Dental Prosthesis For Use in Developing Final Dental Prosthesis", each of which is hereby incorporated by reference herein in its entirety.

FIELD OF THE INVENTION

The present disclosure relates generally to developing a final dental prosthesis. More particularly, the present disclosure relates to using a temporary dental prosthesis in developing a final dental prosthesis.

BACKGROUND OF THE INVENTION

The dental restoration of a partially or wholly edentulous patient with artificial dentition is typically done in two stages. In the first stage, an incision is made through the gingiva to expose the underlying bone. An artificial tooth root, in the form of a dental implant, is placed in the jawbone for osseointegration. The dental implant generally includes a threaded bore to receive a retaining screw for holding mating components thereon. During the first stage, the gum tissue overlying the implant is sutured and heals as the osseointegration process continues.

Once the osseointegration process is complete, the second stage is initiated. Here, the gingival tissue is re-opened to expose an end of the dental implant. A healing component or healing abutment is fastened to the exposed end of the dental implant to allow the gingival tissue to heal therearound. It should be noted that the healing abutment can be placed on the dental implant immediately after the implant has been installed and before osseointegration, thereby, for some situations, combining the osseointegration step and gingival healing step into a one-step process.

Prior healing abutments were generally round in profile, but the artificial teeth or prostheses that eventually replaced the healing abutments were not. Thus, the gingival tissue would heal around the healing abutments creating a gingival emergence profile that approximated the size and contour of the healing abutment and not the size and contour of the final prosthesis that was eventually attached to the implant. The resulting discrepancies between the emergence profile of the patient's gingiva and the installed final prosthesis could sometimes require additional visits with the dentist or clinician to finalize the installation process and/or compromise the aesthetic outcome of the installed final prosthesis (e.g., the visual look of the patient's gingival tissue abutting the final prosthesis). Thus, in recent years, standard healing abutments have been replaced with temporary prosthetic abutments.

Further, implant dentistry restorative methods have advanced beyond requiring a fixture-level (e.g., dental implant level) impression as the starting point for developing a final dental prosthesis. In some such cases pre-defined scan bodies (e.g., Encode Healing Abutments available from Biomet 3i, LLC) are assembled to the dental implants during the gingival healing stage. The pre-defined scan bodies include scannable features (e.g., markers) that, when scanned and interpreted, provide information about the location and orientation of the underlying dental implant that is used in developing the final dental prosthesis.

Although such methods using pre-defined scan bodies provide many benefits (e.g., improved aesthetics, reduced complexity, and potentially accelerated treatment times), such methods are reliant on scanning technology. A need exists for a patient-specific restorative solution that does not require dedicated pre-defined scan bodies as to further reduce the treatment complexity and improve restorative flexibility. The present disclosure is directed to solving these and other needs.

SUMMARY OF THE INVENTION

The present disclosure provides methods for developing and fabricating permanent patient-specific prostheses without needing pre-defined scan bodies. Thus, the methods of the present disclosure can reduce treatment complexity and enhance restorative flexibility, and thereby improve the dental restoration process. In particular, a patient-specific temporary prosthesis (PSTP) is fabricated and then scanned to generate scan data and/or a virtual three-dimensional model of the PSTP that captures all of the contours and details of the PSTP. The PSTP is attached to the implant in the patient's mouth and the gingival tissue is permitted to heal therearound. Subsequently, a clinician determines if the gingival tissue has healed around the PSTP in a desired manner (e.g., aesthetically pleasing manner). If so, a permanent patient-specific prosthesis is created as an exact replica of the PSTP using the scan data and/or the virtual three-dimensional model of the PSTP. If not, depending on the necessary modifications, (i) the PSTP is physically modified and rescanned or (ii) the scan data and/or the virtual three-dimensional model of the PSTP are virtually modified. Then, a permanent patient-specific prosthesis is created as an exact replica of (i) the modified PSTP using scan data and/or a virtual three-dimensional model generated from the rescanning of the modified PSTP or (ii) the virtually modified virtual three-dimensional model of the PSTP. Either way, by scanning the entire PSTP and generating scan data and/or the virtual three-dimensional model of the PSTP: (i) pre-defined scan bodies are not necessary to develop and fabricate the permanent patient-specific prosthesis and (ii) nor are pre-defined scan bodies necessary to determine the location of the implant with respect to the adjacent and/or opposing dentition.

A method of manufacturing a permanent prosthesis for attachment to a dental implant installed in a mouth of a patient includes scanning a patient specific temporary prosthesis (PSTP) to obtain scan data. The PSTP is attached to the dental implant in the mouth of the patient. Gingival tissue surrounding the PSTP is permitted to heal in the mouth of the patient. In response to the aesthetics of the healed gingival tissue surrounding the PSTP in the mouth of the patient being acceptable, the permanent prosthesis is manufactured as a replica of the PSTP using the obtained scan data.

A method of manufacturing a permanent prosthesis for attachment to a dental implant installed in a mouth of a patient includes scanning a patient specific temporary prosthesis (PSTP) to obtain scan data. The PSTP is attached to the dental implant in the mouth of the patient. Gingival tissue surrounding the PSTP is permitted to heal in the mouth of the patient. In response to the aesthetics of the healed gingival tissue surrounding the PSTP in the mouth of the patient not being acceptable, the PSTP is physically modified by (i) removing material from the PSTP, (ii) adding material to the PSTP, or (iii) both.

A method of manufacturing a permanent prosthesis for attachment to a dental implant installed in a mouth of a patient includes generating scan data from a scan of a patient specific temporary prosthesis (PSTP). Subsequent to the PSTP being attached to the dental implant in the mouth of the patient and gingival tissue surrounding the PSTP being permitted to heal in the mouth of the patient, modified scan data is generated from a scan of a physically modified PSTP. The PSTP is physically modified in response to the aesthetics of the healed gingival tissue surrounding the PSTP in the mouth of the patient not being acceptable.

A method of manufacturing a permanent prosthesis includes acquiring scan data including computed tomography (CT) data, intraoral scan (IOS) data, or both, of a mouth of patient. Using the scan data, a location in the mouth of the patient is determined to install a dental implant. Using the scan data and the determined location in the mouth of the patient to install the dental implant, a patient specific temporary prosthesis (PSTP) is virtually designed and virtual PSTP data is generated. Using the virtual PSTP data, the PSTP is manufactured. The dental implant is installed in the mouth of the patient substantially at the determined location. The manufactured PSTP is attached to the dental implant installed in the mouth of the patient. Gingival tissue surrounding the PSTP is permitted to heal in the mouth of the patient. In response to the aesthetics of the healed gingival tissue surrounding the PSTP in the mouth of the patient being acceptable, the permanent prosthesis is manufactured as a replica of the PSTP using the virtual PSTP data.

A method of manufacturing a permanent prosthesis includes acquiring scan data including computed tomography (CT) data, intraoral scan (IOS) data, or both, of a mouth of patient. Using the scan data, a location in the mouth of the patient is determined to install a dental implant. Using the scan data and the determined location in the mouth of the patient to install the dental implant, a patient specific temporary prosthesis (PSTP) is virtually designed and virtual PSTP data is generated. Using the virtual PSTP data, the PSTP is manufactured. The dental implant is installed in the mouth of the patient substantially at the determined location. The manufactured PSTP is attached to the dental implant installed in the mouth of the patient. Gingival tissue surrounding the PSTP is permitted to heal in the mouth of the patient. In response to the aesthetics of the healed gingival tissue surrounding the PSTP in the mouth of the patient not being acceptable, the PSTP is physically modified by (i) removing material from the PSTP, (ii) adding material to the PSTP, or (iii) both.

Additional aspects of the present disclosure will be apparent to those of ordinary skill in the art in view of the detailed description of various implementations, which is made with reference to the drawings, a brief description of which is provided below.

BRIEF DESCRIPTION OF THE DRAWINGS

The foregoing and other advantages of the disclosure will become apparent upon reading the following detailed description and upon reference to the drawings.

Figure 1A:
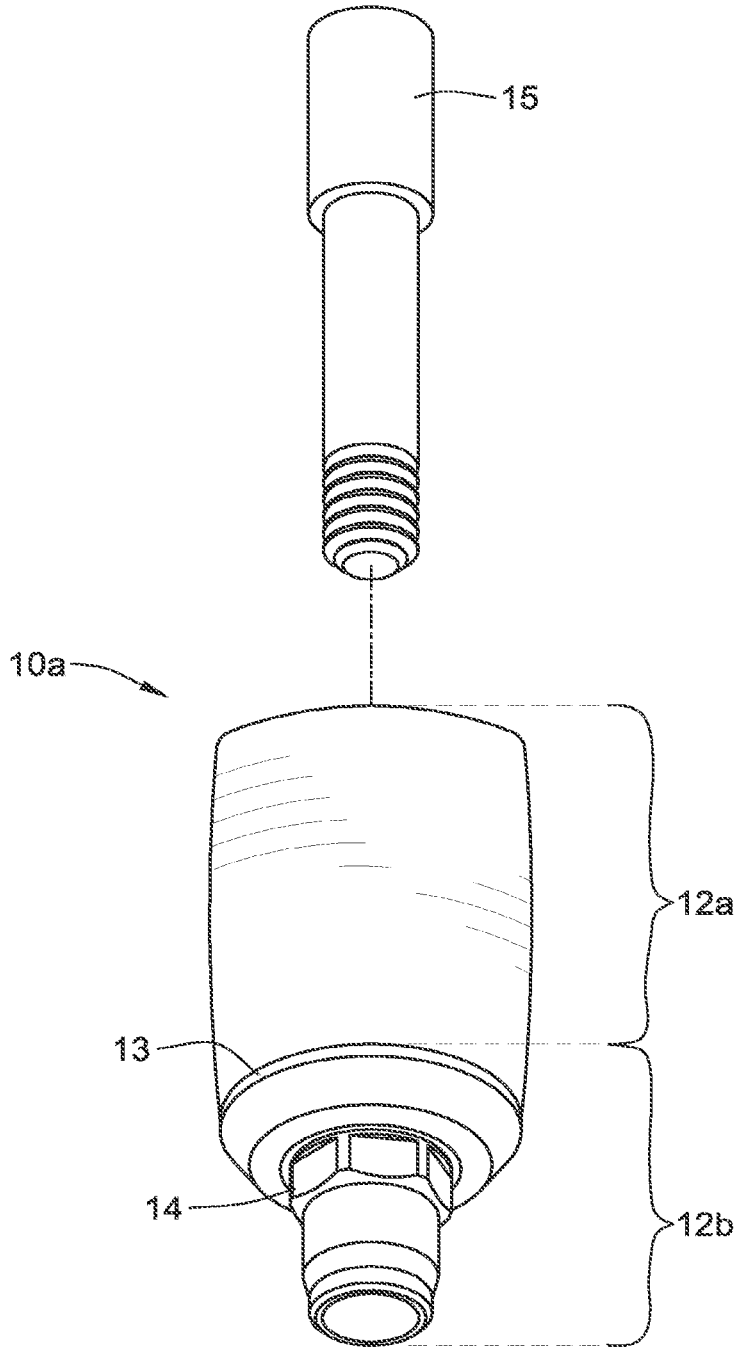
FIG. 1A is a perspective view of a one-piece temporary prosthesis according to some aspects of the present disclosure.

While the present disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DESCRIPTION OF ILLUSTRATIVE EMBODIMENTS

Figure 1B:
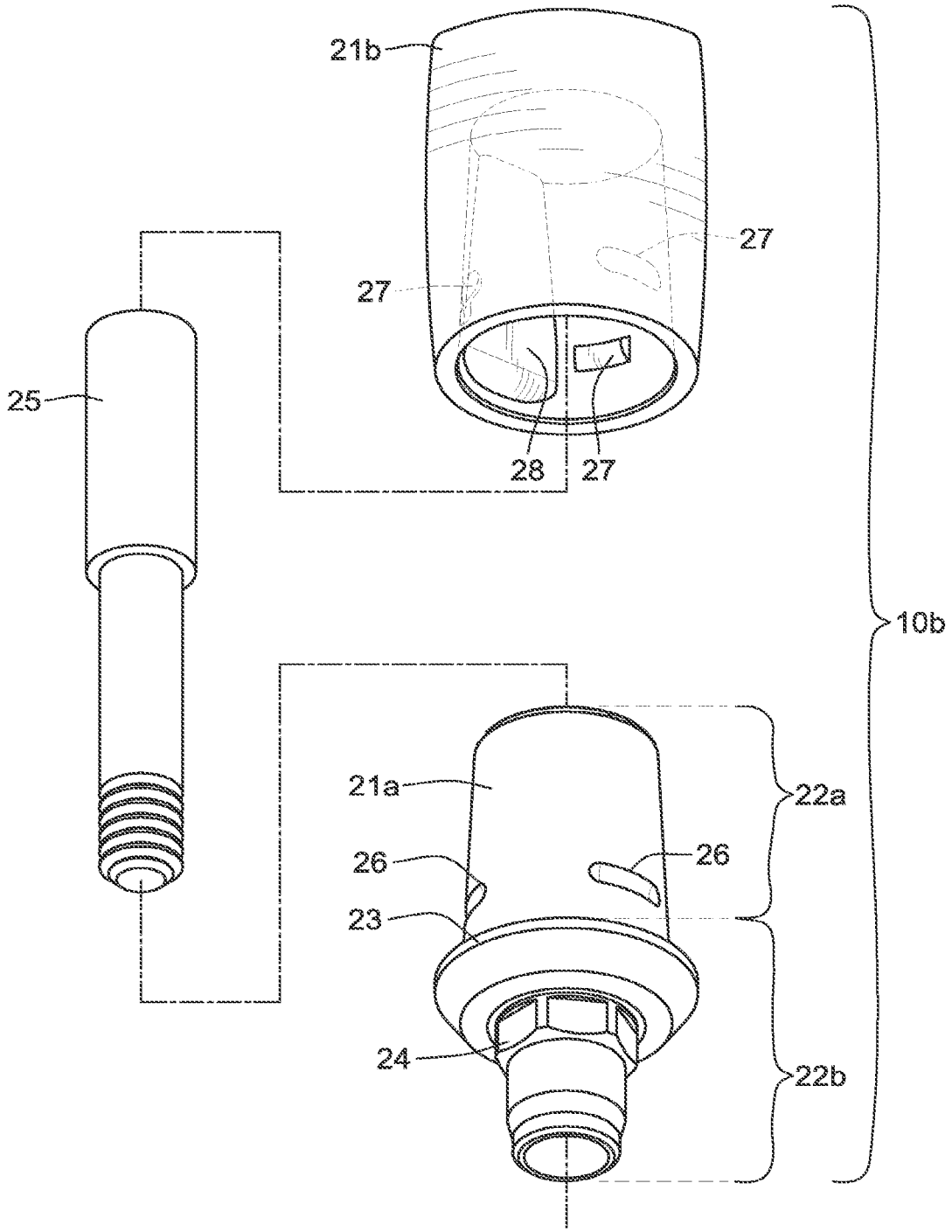
FIG. 1B is a perspective view of a two-piece temporary prosthesis according to some aspects of the present disclosure.
Figure 1C:
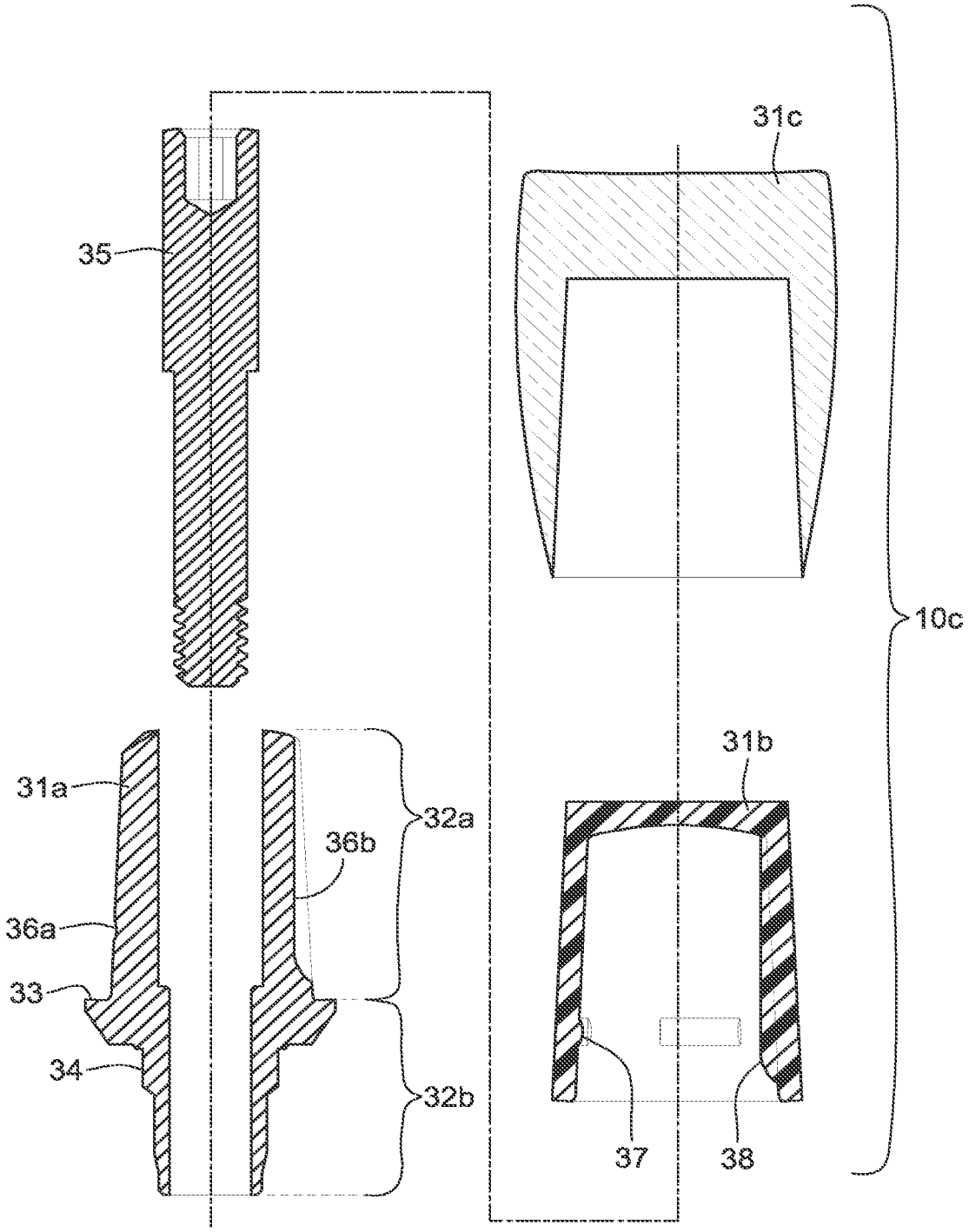
FIG. 1C is a cross-sectional view of a three-piece temporary prosthesis according to some aspects of the present disclosure.

Referring to FIGS. 1A, 1B, and 1C, patient-specific temporary prostheses ("PSTPs") 10a, 10b, and 10c are used to develop final or permanent patient-specific prostheses in accordance with the present disclosure. Further, the PSTPs 10a, 10b, and 10c serve as gingival healing abutments as their exterior surfaces are contoured to aid in the healing of a patient's gingival tissue.

Referring specifically to FIG. 1A, the PSTP 10a has a supragingival region 12a and a subgingival region 12b, which are separated by a flange 13. The PSTP 10a is a one-piece prosthesis in that the supragingival region 12a and the subgingival region 12b are formed from the same material (e.g., acrylic). Alternatively, the supragingival region 12a is permanently attached to the subgingival region 12b making the PSTP a one-piece prosthesis. In such an alternative, the supragingival region 12a can be made of a first material (e.g., acrylic) and the subgingival region 12b can be made of a second material (e.g., metal, such as titanium).

Figure 2:
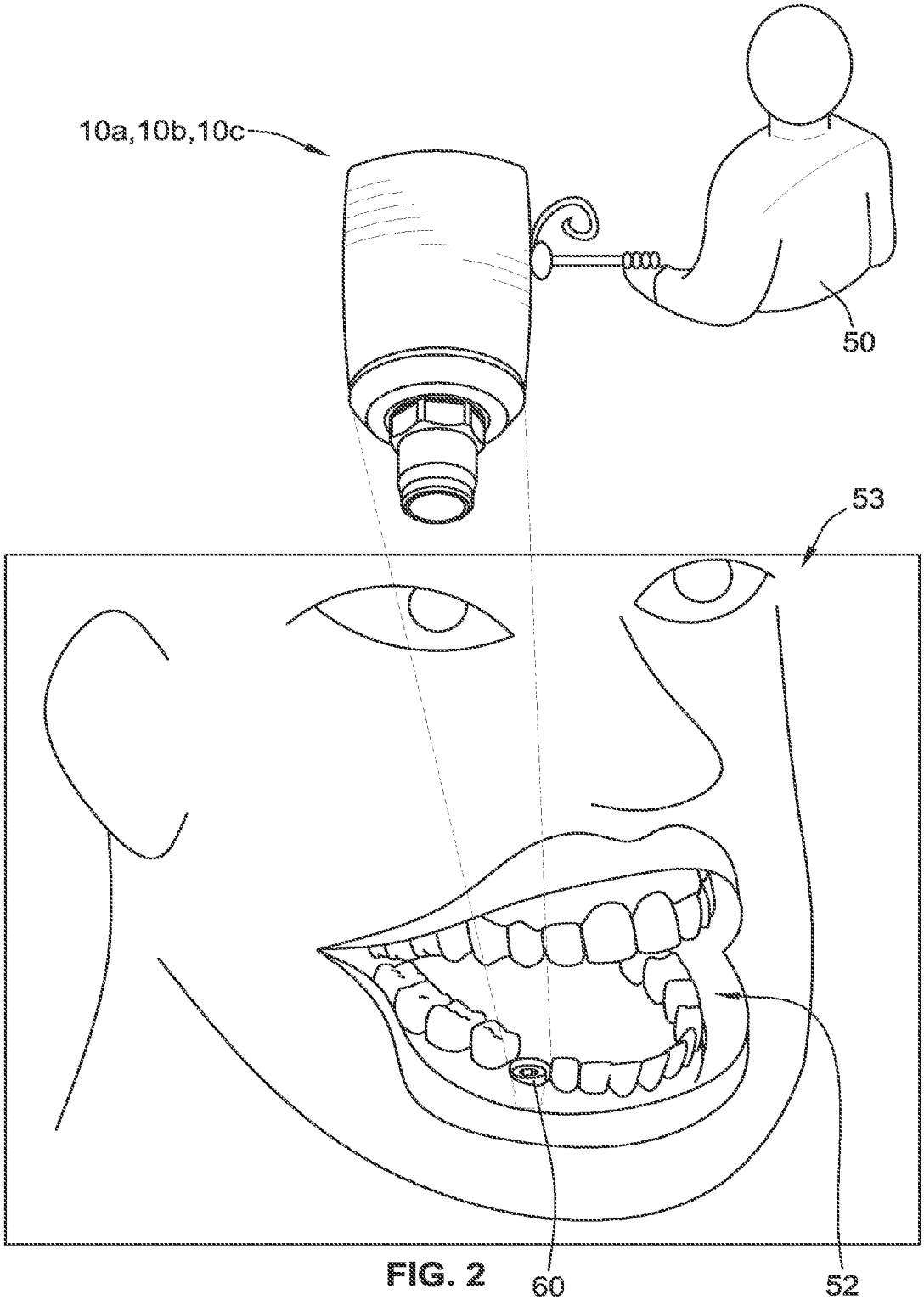
FIG. 2 is a depiction of a clinician manually modifying a temporary prosthesis prior to installing the same in to a mouth of a patient according to some aspects of the present disclosure.

The subgingival region 12b includes an anti-rotational feature 14 (e.g., a hexagonal section) for mating with a corresponding anti-rotational feature of an implant (e.g., implant 60 in FIG. 2). The PSTP 10a is held onto the implant 60 using a retaining screw 15. The anti-rotational feature 14 of the PSTP 10a can be any type of boss (e.g., polygonal boss, star boss, clover boss, etc.) or socket (e.g., polygonal socket, star socket, clover socket, etc.) such that it corresponds with an anti-rotational feature of the underlying implant 60 to prevent relative rotation of the PSTP 10a with respect to the implant 60. It is contemplated that the PSTP 10a (and the other PSTPs of the present disclosure) can be fashioned from gold, titanium, plastic, ceramic, acrylic, or other similar metals or composites, or any combination thereof.

Referring specifically to FIG. 1B, the PSTP 10b is similar to the PSTP 10a, except that the PSTP 10b is a two-piece prosthesis. That is, the PSTP 10b includes a temporary abutment 21a and a temporary abutment cap 21b (e.g., temporary crown). The temporary abutment cap 21b is removable from the temporary abutment 21a (e.g., in a snap-like fashion and/or in a sliding-like fashion) such that a screw 25 can attach the temporary abutment 21a to the implant 60 and the temporary abutment cap 21b can then be attached to the temporary abutment 21a thereafter.

The temporary abutment 21a has a supragingival region 22a and a subgingival region 22b, which are separated by a flange 23. The subgingival region 22b includes an anti-rotational feature 24 (the same as, or similar to, the anti-rotational feature 14) for mating with a corresponding anti-rotational feature of the implant 60. The supragingival region 22a of the temporary abutment 21a includes one or more retention grooves or structures 26 and an anti-rotational structure (e.g., a flat wall or surface) that is not shown. The retention grooves 26 are configured to mate in a snap-type axial holding engagement with corresponding male circumferential features or structures 27 of the temporary abutment cap 21b. Alternatively to the temporary abutment 21a including retention grooves 26 and the temporary abutment cap 21b including corresponding male circumferential features, dental cement, or the like, can be used to mate (e.g., hold together) the temporary abutment 21a with the temporary abutment cap 21b.

The anti-rotational structure (not shown) of the temporary abutment 21a is configured to mate in a slideable engagement with a corresponding anti-rotational structure 28 to prevent relative rotation of the temporary abutment cap 21b and the temporary abutment 21a. In the illustrated implementation, the anti-rotational structure (not shown) generally extends from a top surface of the temporary abutment 21a to the flange 23. Details on and examples of anti-rotational structures for dental posts (e.g., supragingival regions of temporary abutments) are shown in U.S. Pat. Nos. 6,120,293, 6,159,010, and 8,002,547, each of which is commonly owned by the assignee of the present application and is hereby incorporated by reference herein in its entirety.

Referring specifically to FIG. 1C, the PSTP 10c is similar to the PSTPs 10a and 10b, except that the PSTP 10c is a three-piece prosthesis. That is, the PSTP 10c includes a temporary abutment 31a, a temporary abutment cap 31b, and a temporary crown 31c. The temporary abutment cap 31b is removable from the temporary abutment 31a (e.g., in a snap-like fashion and/or in a sliding-like fashion) such that a screw 35 can attach the temporary abutment 31a to the implant 60 and the temporary abutment cap 31b can then be attached to the temporary abutment 31a thereafter. Further, the temporary crown 31c is mated with and/or bonded to the temporary abutment cap 31b prior to, or after, the temporary abutment cap 31b is attached to the temporary abutment 31a. It is contemplated that the temporary crown 31c is coupled to the temporary abutment cap 31b using cement (e.g., dental cement), glue, bonding agent, a press-fit engagement, a snap or click-type engagement, a screw or bolt, or a combination thereof.

The temporary abutment 31a has a supragingival region 32a and a subgingival region 32b, which are separated by a flange 33. The subgingival region 32b includes an anti-rotational feature 34 (the same as, or similar to, the anti-rotational features 14, 24) for mating with a corresponding anti-rotational feature of the implant 60. The supragingival region 32a of the temporary abutment 31a includes one or more retention grooves or structures 36a and an anti-rotational structure 36b (e.g., a flat wall or surface). The retention grooves 36a are configured to mate in a snap-type axial holding engagement with corresponding male circumferential features or structures 37 of the temporary abutment cap 31b.

The anti-rotational structure 36b of the temporary abutment 31a is configured to mate in a slideable engagement with a corresponding anti-rotational structure 38 to prevent relative rotation of the temporary abutment cap 31b and the temporary abutment 31a. In the illustrated implementation, the anti-rotational structure 36b generally extends from a top surface of the temporary abutment 31a to the flange 33.

Additional details on, and examples of, temporary abutments and/or PSTPs are shown and described in U.S. patent application Ser. No. 13/473,219, filed on May 16, 2012, which is commonly owned by the assignee of the present application and is hereby incorporated by reference herein in its entirety.

Referring to FIG. 2, a clinician 50 is shown manually modifying and/or customizing the PSTP 10a, 10b, 10c prior to installing the same in a mouth 52 of a patient 53. That is, one way for the PSTPs 10a, 10b, and 10c to be fabricated is by a clinician removing and/or adding material to a stock or standard temporary prosthetic to create one of the PSTPs 10a, 10b, 10c. The stock or standard PSTP can have an anatomical tooth shape or a non-anatomical tooth shape (e.g., cylindrical, square, etc.). Such a manual method can be accomplished chair side after the implant 60 is installed into the patient's mouth 52 such that the patient 53 can leave with a PSTP 10a, 10b, 10c acting as a temporary tooth and as a gingival healing abutment immediately after the implant 60 is installed.

In some implementations of the present concepts, a kit or package of PSTPs can be supplied to the clinician, where each of the PSTPs in the kit has a preformed anatomical tooth shape of a predetermined size and shape. The clinician can select the appropriate PSTP and begin modifications as necessary for the particular patient. Thus, in such implementations, the clinician is supplied with a variety of preformed PSTPs having different anatomical teeth shapes that can be modified/customized as necessary and attached to the implant 60.

Figure 3:
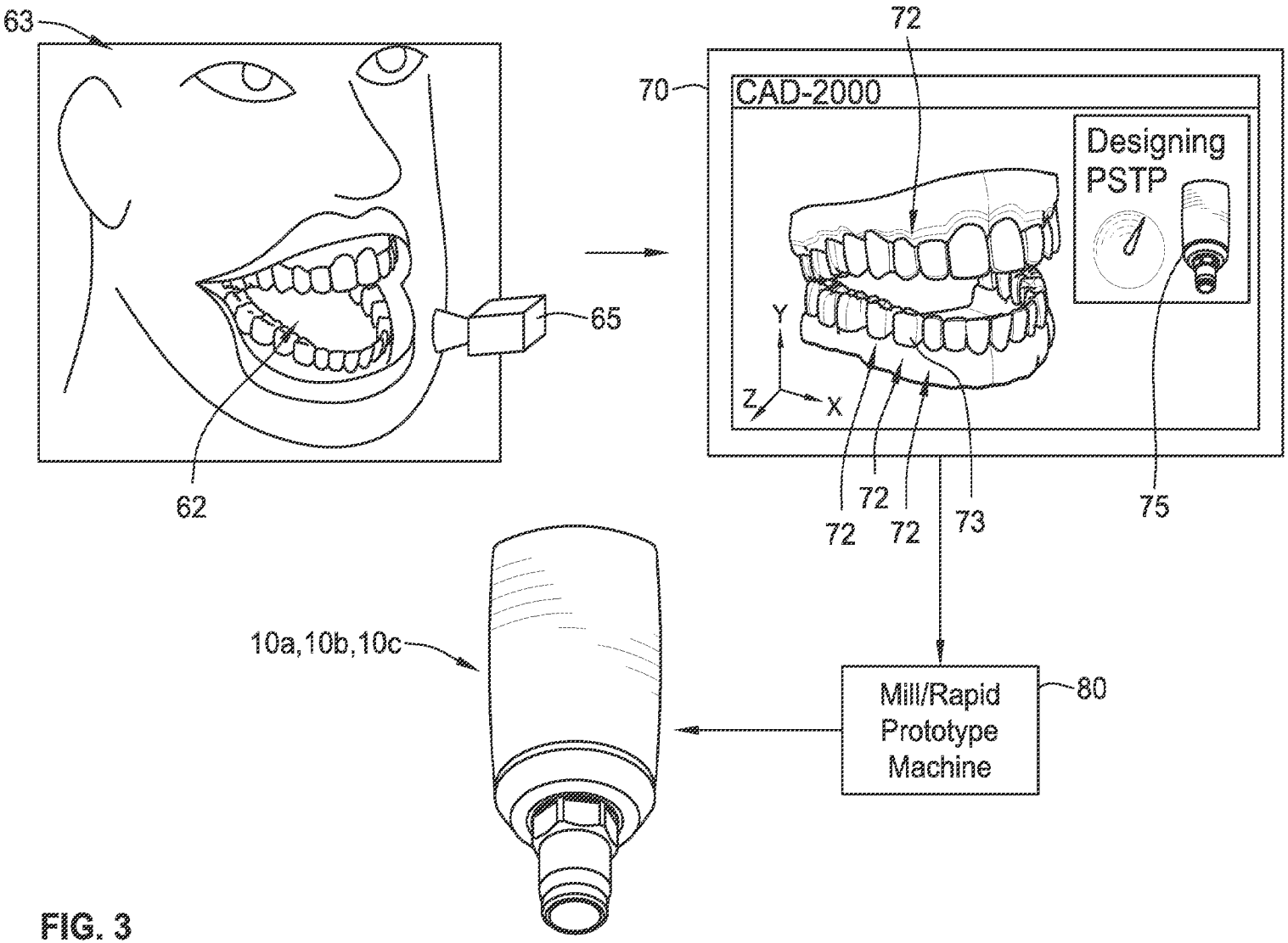
FIG. 3 is an animated flow chart illustrating a virtual design and fabrication of a temporary prosthesis according to some aspects of the present disclosure.

Alternatively to the manual method described in reference to FIG. 2, referring to FIG. 3, the PSTPs 10a, 10b, 10c can be virtually/digitally designed and fabricated using a milling machine (e.g., a 5 axis milling machine) and/or a rapid prototype machine 80 prior to the implant 60 being installed into a mouth 62 of a patient 63. As shown in FIG. 3, prior to any implants being installed, a computed tomography ("CT") scan and/or an intraoral scan (IOS) can be taken of the mouth 62 of the patient 63 using one or more scanners/cameras 65 (e.g., e-ray scanners, etc.). Scan data and/or virtual three-dimensional models generated from the CT and/or IOS scans is transferred to a computer system 70 including software (e.g., CAD software, graphical imaging software, etc.) configured to process the generated scan data and/or virtual three-dimensional models and virtually design a PSTP for the patient 63. Specifically, the software evaluates the scan data and/or virtual three-dimensional models associated with the teeth and the gingival tissue 72 of the patient 63 surrounding and adjacent to the planned implant site 73 (e.g., site where a tooth will be removed and replaced with an implant) and accordingly designs a virtual PSTP 75. After the virtual PSTP 75 is designed, virtual temporary prosthesis data is generated. The virtual temporary prosthesis data includes instructions for the milling and/or rapid prototype machine 80 to execute in order to fabricate the PSTP (e.g., the PSTPs 10a, 10b, 10c). Additional details on rapid prototyping in general can be found in U.S. Pat. No. 8,185,224, which is hereby incorporated by reference herein in its entirety. Additional details on creating bone and soft-tissue digital dental models (e.g., virtual three-dimensional models) from the CT scan and the IOS scan can be found in U.S. Patent Application Publication No. 2011/0129792, which is hereby incorporated by reference herein in its entirety.

Whether the PSTP is manually modified (FIG. 2) and/or designed and fabricated using a milling and/or rapid prototype machine (FIG. 3), the outer surfaces of the PSTPs 10a, 10b, 10c are configured to be suitable for replicating the gingival emergence profile formed by a natural tooth (e.g., in a non-round shape). As such, after the PSTPs 10a, 10b, 10c are installed (e.g., attached to the implant 60) in the mouth of the patient, the patient's gingiva is permitted to heal around the PSTP 10a, 10b, 10c, which results in a gingival emergence profile approximating that of what would be around a natural tooth. In other words, the PSTP 10a, 10b, 10c also acts as a gingival healing abutment.

Figure 4:
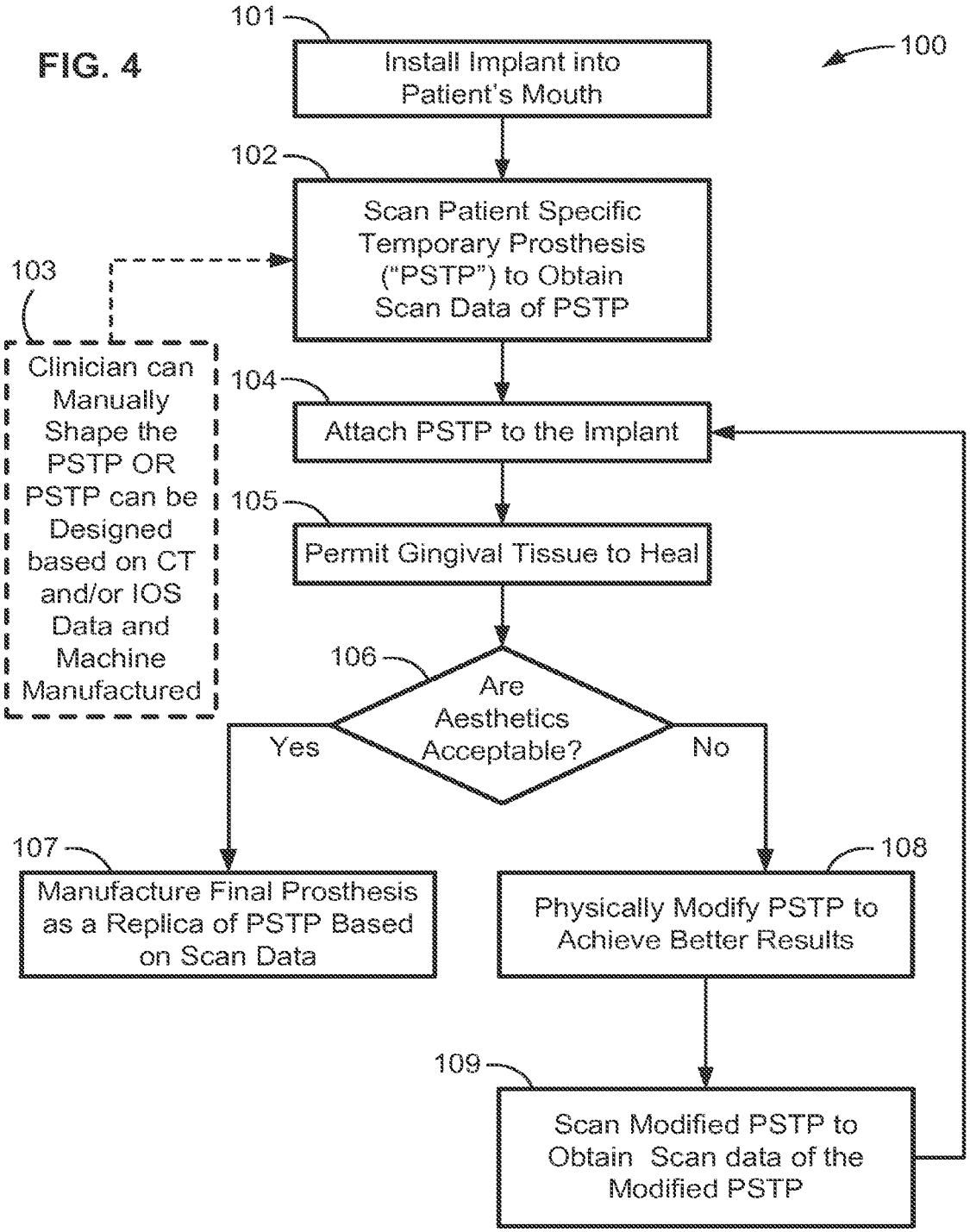
FIGS. 4-9 are flow charts of various methods for manufacturing a permanent prosthesis.

Now referring to FIG. 4, a method 100 of manufacturing a permanent patient-specific prosthesis (e.g., a final prosthesis) for attachment to a dental implant (e.g., implant 60) installed in a mouth of a patient is described in reference to a flow chart. Initially, a dental implant (e.g., implant 60) is installed into the mouth of a patient (101). A PSTP, to be attached to the implant 60, is scanned to obtain scan data of the PSTP (102) and/or a virtual three-dimensional model of the PSTP. The scanned PSTP can be manually formed and/or modified by a clinician as described in reference to FIG. 2, or the scanned PSTP can be designed virtually based on CT and/or IOS data and machine manufactured as described in reference to FIG. 3 (103). The PSTP can be scanned using any type or kind of scanner, such as, for example, a 3D dental scanner (e.g., model nos. D500, D700, D710, D800, and D810) available from 3Shape A/S located in Copenhagen, Denmark or a LAVA Chairside Oral Scanner available from 3M located in Saint Paul, Minn. The scanning of the PSTP generates the scan data associated with the PSTP that can be used to create a virtual three-dimensional model of the PSTP. Thus, the scanning of the PSTP captures all of the contours, sizes, and shapes of the PSTP in a digital format that can be displayed as a virtual three-dimensional model of the PSTP on a display device (e.g., computer monitor). Specifically, the entire PSTP is scanned such that the virtual three-dimensional model of the PSTP is a complete virtual replica of the PSTP.

After the PSTP is scanned and the scan data is obtained (102), the PSTP is attached to the dental implant (104). In some implementations, the PSTP is attached to the dental implant in a non-rotational fashion (e.g., using complementary non-rotational features) and held in place using a screw fastener (e.g., screw 15, 25, 35). After the PSTP is attached to the implant (104), the patient's gingival tissue is permitted to heal around the PSTP (105). The gingival tissue generally heals in a shape with an emergence contour profile that corresponds to the external contours of the PSTP abutting the gingival tissue.

After the gingival tissue is permitted to heal (105) for a predetermined amount of time (e.g., a day, two weeks, a month, three months, six months, a year, etc.), the aesthetics of the gingival tissue surrounding the PSTP are checked to determine if the aesthetics of the gingival tissue surrounding the PSTP are acceptable (106). By acceptable, it is meant that the gingival tissue is hugging the PSTP in an aesthetically pleasing manner as determined by, for example, a clinician treating the patient. It is also contemplated that in an alternative implementation, the aesthetics can be determined to be acceptable by a computer executing software that analyzes scan data and/or a virtual three-dimensional model generated from a scan of the patient's mouth including the gingival tissue surrounding the PSTP after healing has occurred. Additionally, the aesthetics of the PSTP itself can be checked to determine, for example, if the aesthetics of the supragingival portion of the PSTP are acceptable (e.g., match the size, shape, and/or color of a natural tooth in view of the surrounding teeth).

If the aesthetics of the gingival tissue and/or of the PSTP itself are determined to be acceptable (106), a final prosthesis is manufactured as a replica of the PSTP based on the scan data (107) and/or the virtual three-dimensional model of the PSTP. That is, the scan data from the scan of the PSTP (102) is used to create an actual and physical replica of the PSTP using, for example, a milling machine and/or a rapid-prototype machine. Thus, the outer contours of the final prosthesis are the same as, or substantially the same as, the outer contours of the PSTP. The final prosthesis can be made of gold, titanium, plastic, ceramic, acrylic, porcelain, or other similar metals or composites, or any combination thereof.

Essentially, the difference between the PSTP and the final prosthesis are the materials that are used and/or the mechanical configuration which is employed to make the PSTP and the final prosthesis. Generally, in some implementations, the PSTP is made of plastic and the final prosthesis is made of a titanium insert with a ceramic crown having a porcelain coating thereon. Thus, in some implementations, the PSTP is physically softer (e.g., easier to modify and relatively less durable) and the final prosthesis is physically harder (harder to modify and relatively more durable) and more aesthetically pleasing (including color and/or shading). By different mechanical configuration it is meant that while the outer contours of the final prosthesis match the outer contours of the PSTP, the final prosthesis can be formed by a different number of subparts or portions as compared to the PSTP. For example, the PSTP can be formed as a unitary piece of plastic and the final prosthesis can be formed by a metal abutment and a ceramic crown attached thereto.

If the aesthetics are determined to not be acceptable (106), the PSTP is physically modified to achieve better results (108). That is, after additional healing of the gingival tissue is permitted about the physically modified PSTP, better aesthetic results are expected due to the modifications of the PSTP. The PSTP can be manually modified by the clinician treating the patient. Alternatively, the PSTP can be modified using a milling machine and/or a rapid prototype machine. The modifications can be made to the PSTP with the PSTP installed in the patient's mouth and/or with the PSTP removed therefrom. The modifications can include removal of material from the PSTP, additional material being added to the PSTP, material of the PSTP being moved/deformed (e.g., bent, twisted, etc.), or any combinations thereof.

After the PSTP is physically modified (108), the modified PSTP is scanned to obtain scan data of the modified PSTP (109) and/or a virtual three-dimensional model of the modified PSTP. The scan data obtained from the modified PSTP essentially replaces the scan data obtained from the unmodified PSTP described above. The modified PSTP can be scanned (109) in the same, or similar, manner that the unmodified PSTP was scanned (102) described above. After the modified PSTP is scanned (109), the PSTP is reattached to the implant (104) and acts (105), (108), and (109) are repeated until the aesthetics are found to be acceptable (106) and then the final prosthesis is manufactured (107) based on the latest scan data from a scan of the latest modified PSTP.

Figure 5:
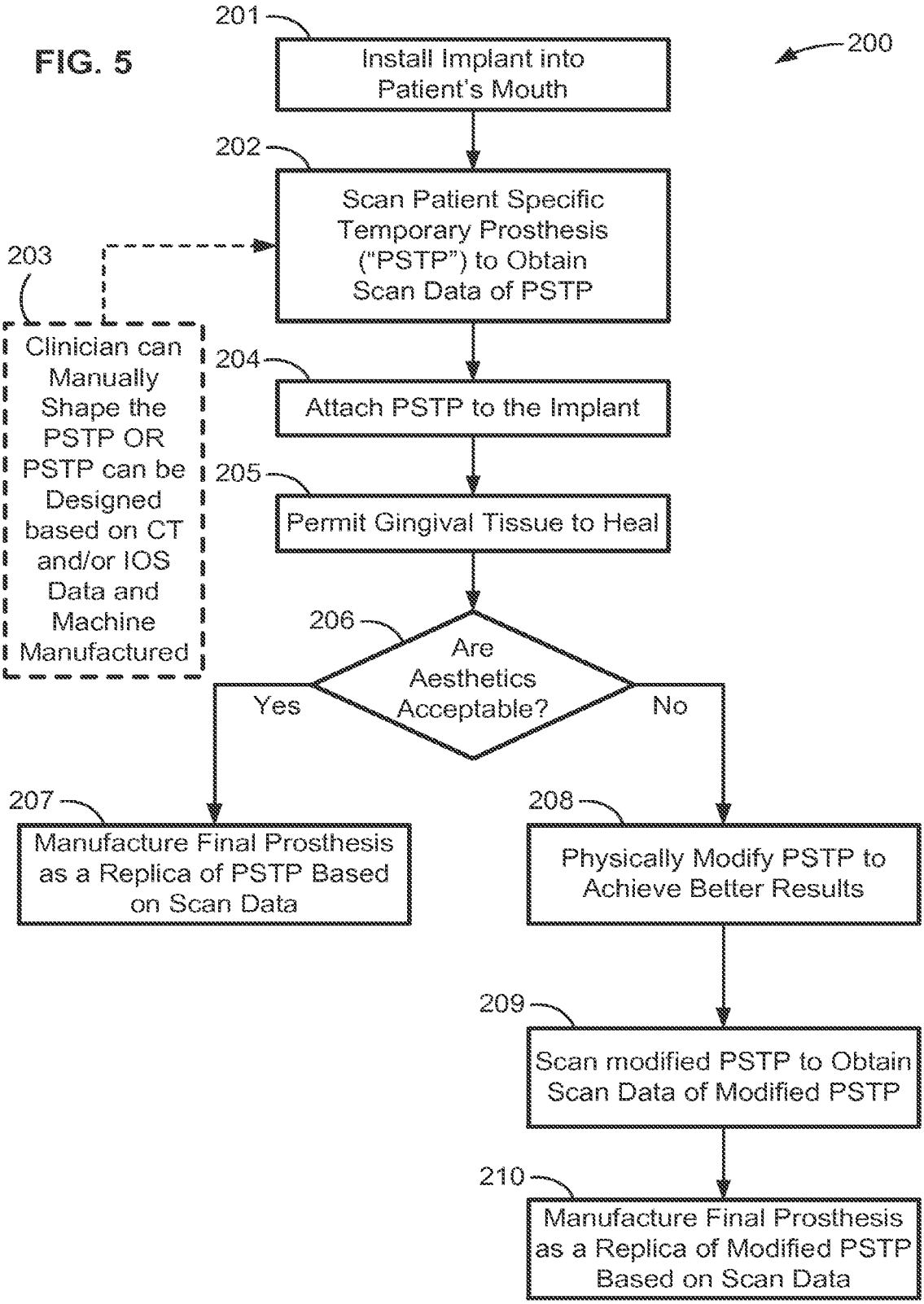

Now referring to FIG. 5, a method 200 of manufacturing a permanent patient-specific prosthesis (e.g., a final prosthesis) for attachment to a dental implant (e.g., implant 60) installed in a mouth of a patient is described in reference to a flow chart. The method 200 includes acts (201)-(209) which are the same as acts (101)-(109) described above in reference to the method 100 of FIG. 4. However, the method 200 further includes act (210) after the modified PSTP is scanned (209). After the modified PSTP is scanned (209), the final prosthesis is manufactured as a replica of the modified PSTP based on the scan data and/or the virtual three-dimensional model from the scan of the modified PSTP (210) without rechecking the aesthetics as in the method 100. That is, in the method 200, the aesthetics are not rechecked after the modifications to the PSTP (208). Foregoing the rechecking of the aesthetics in the method 200 may accelerate the treatment time for the patient as compared to the method 100. A clinician might forego the rechecking of the aesthetics when the modifications to the PSTP are minor and/or supragingival (e.g., modifications are made to the portion of the PSTP not abutting or blocked by the gingival tissue).

Figure 6:
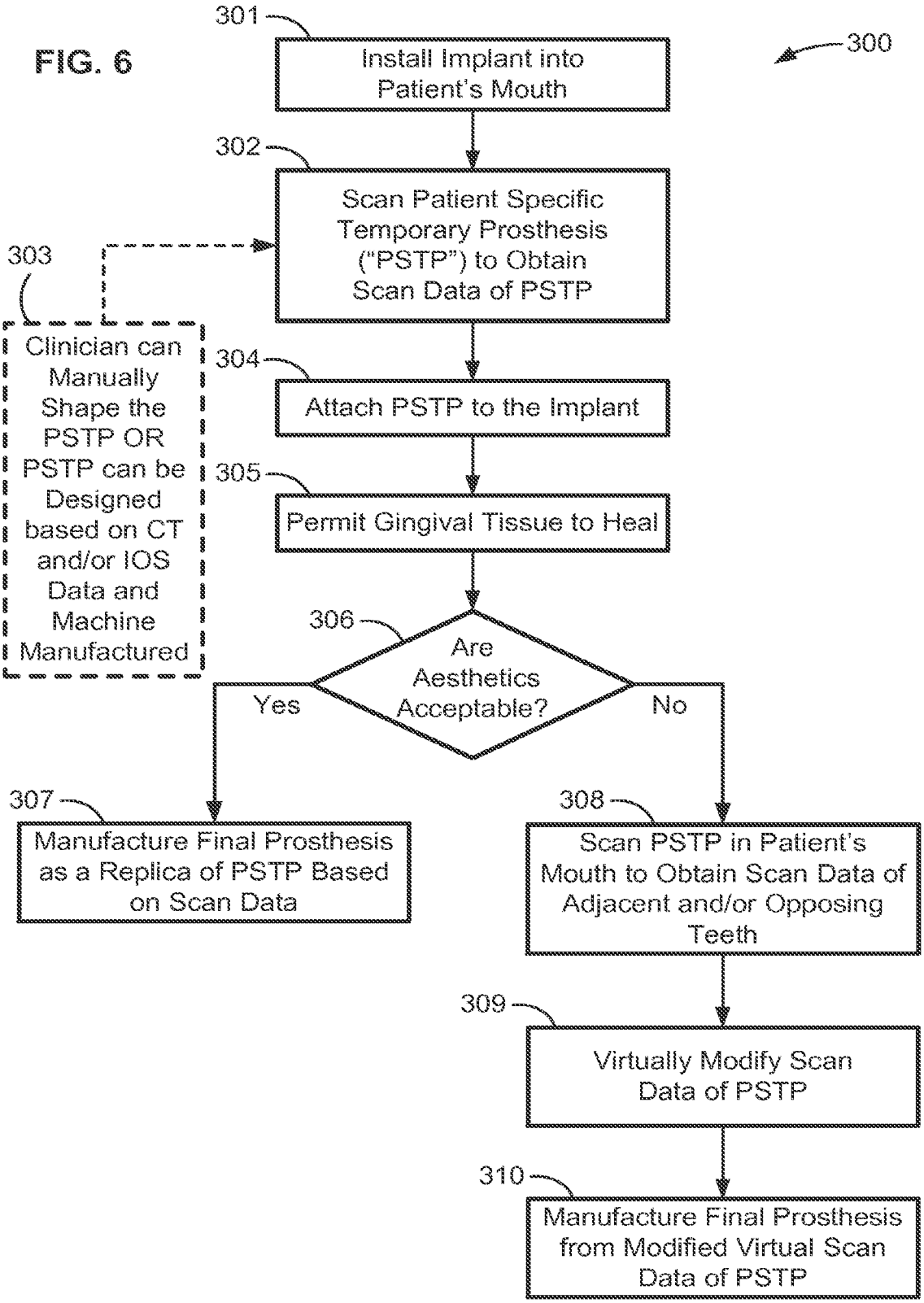

Now referring to FIG. 6, a method 300 of manufacturing a permanent patient-specific prosthesis (e.g., a final prosthesis) for attachment to a dental implant (e.g., implant 60) installed in a mouth of a patient is described in reference to a flow chart. The method 300 includes acts (301)-(307) which are the same as acts (101)-(107) described above in reference to the method 100 of FIG. 4. However, the method 300 replaces acts (108) and (109) with acts (308), (309), (310) in response to the aesthetics being determined to not be acceptable (306).

If the aesthetics are determined to not be acceptable (306), the patient's mouth (or a portion of the patient's mouth) is scanned to obtain additional scan data (308) and/or a virtual three-dimensional model of at least a portion of the patient's mouth. In some implementations, the installed PSTP, the adjacent gingival tissue healing therearound, and adjacent and/or opposing teeth are scanned to generate scan data and/or a virtual three-dimensional model of the PSTP, the adjacent gingival tissue, and the adjacent and/or opposing teeth. Then, the originally obtained scan data and/or the virtual three-dimensional model of the PSTP are virtually modified (309). Specifically, the scan data and/or the virtual three-dimensional model of the PSTP are virtually modified by the clinician treating the patient and/or another designer. The virtual modifications can be made to the scan data and/or the virtual three-dimensional model of the PSTP with the PSTP remaining in the patient's mouth (e.g., the PSTP does not need to be removed for the virtual modification). The virtual modifications can include virtually removing material from the virtual three-dimensional model of the PSTP and/or virtually adding material to the virtual three-dimensional model of the PSTP. A clinician might virtually modify the scan data of the PSTP (instead of physically modifying the PSTP) when the modifications to the PSTP are minor (e.g., the modifications will not significantly impact the healing of the gingival tissue) and/or supragingival (e.g., modifications are made to the portion of the PSTP not abutting or blocked by the gingival tissue).

After the scan data and/or the virtual three-dimensional model of the PSTP are virtually modified (309), the final prosthesis is manufactured as a replica of the virtually modified virtual three-dimensional model of the PSTP (310). Specifically, the final prosthesis is manufactured based on the virtually modified scan data of the PSTP (310) without rechecking the aesthetics as in the method 100 and without physically modifying the PSTP installed in the mouth of the patient as in the method 200. That is, in the method 300, the aesthetics are not rechecked after the virtual modifications to the scan data of the PSTP (309) and the PSTP installed in the mouth of the patient is not physically modified. As described above, foregoing the rechecking of the aesthetics in the method 300 may accelerate the treatment time for the patient as compared to the method 100. Additionally, foregoing the physical modification to the PSTP avoids and/or reduces potential discomfort and tissue remodeling of the patient resulting from having to endure removal of and replacement of the PSTP during such physical modifications.

Several alternative implementations which are similar to the methods 100, 200, and 300 are described below. According to a first alternative, a method of manufacturing a permanent patient-specific prosthesis (e.g., a final prosthesis) for attachment to a dental implant (e.g., implant 60) installed in a mouth of a patient includes installing a dental implant into the mouth of the patient. Then a PSTP is fabricated. The fabricated PSTP is scanned in its entirety generating scan data and/or a virtual three-dimensional model of the PSTP. Then the PSTP is attached to the implant installed in the patient's mouth. The gingival tissue is permitted to heal and then a clinician assesses the site (e.g., visually inspects the site) to determine if any modifications are necessary to the PSTP and/or the final prosthesis design. If no modification(s) are necessary, the final prosthesis is designed and fabricated as a replica of the PSTP (e.g., a copymill) using the scan data and/or the virtual three-dimensional model of the PSTP from the scan of the PSTP (e.g., the final prosthesis includes a titanium abutment with a porcelain coated ceramic crown). The PSTP is removed and the final prosthesis is attached to the implant.

According to a second alternative, a method of manufacturing a permanent patient-specific prosthesis (e.g., a final prosthesis) for attachment to a dental implant (e.g., implant 60) installed in a mouth of a patient includes installing a dental implant into the mouth of the patient. Then a PSTP is fabricated. The fabricated PSTP is scanned in its entirety generating scan data and/or a virtual three-dimensional model of the PSTP. Then the PSTP is attached to the implant installed in the patient's mouth. Then the final prosthesis is designed and fabricated as a replica of the PSTP (e.g., a copymill) using the scan data and/or the virtual three-dimensional model of the PSTP from the scan of the PSTP (e.g., the final prosthesis includes a titanium abutment with a porcelain coated ceramic crown). The gingival tissue is permitted to heal and then the PSTP is removed and the final prosthesis is attached to the implant. In such an implementation, the clinician does not assess the site (e.g., visually inspects the site) to determine if any modifications are necessary to the PSTP and/or the final prosthesis design as the final prosthesis is designed and fabricated without waiting for the gingival tissue to heal.

According to a third alternative, a method of manufacturing a permanent patient-specific prosthesis (e.g., a final prosthesis) for attachment to a dental implant (e.g., implant 60) installed in a mouth of a patient includes installing a dental implant into the mouth of the patient. Then a PSTP is fabricated and attached to the implant installed in the patient's mouth. The gingival tissue is permitted to heal. After healing, the PSTP is removed and the PSTP is scanned in its entirety generating scan data and/or a virtual three-dimensional model of the PSTP. Then the PSTP is reattached to the implant. The final prosthesis is designed and fabricated as a replica of the PSTP (e.g., a copymill) using the scan data and/or the virtual three-dimensional model of the PSTP from the scan of the PSTP (e.g., the final prosthesis includes a titanium abutment with a porcelain coated ceramic crown). The PSTP is removed and the final prosthesis is attached to the implant. Thus, in such an alternative, the PSTP is scanned after gingival tissue healing has occurred and is not scanned prior to the PSTP being initially attached to the implant.

According to a fourth alternative, a method of manufacturing a permanent patient-specific prosthesis (e.g., a final prosthesis) for attachment to a dental implant (e.g., implant 60) installed in a mouth of a patient includes installing a dental implant into the mouth of the patient. Then a PSTP is fabricated. The fabricated PSTP is scanned in its entirety generating scan data and/or a virtual three-dimensional model of the PSTP. Then the PSTP is attached to the implant installed in the patient's mouth. After the PSTP is attached to the implant, the mouth of the patient is scanned. Specifically, the attached PSTP and the adjacent and/or opposing teeth are scanned generating additional scan data and/or a virtual three-dimensional model of the attached PSTP and the adjacent and/or opposing teeth of the patient. The additional scan data and the scan data generated from the scan of the entire PSTP can be merged into a merged dataset and/or a merged virtual three-dimensional model. The gingival tissue is permitted to heal and then a clinician assesses the site (e.g., visually inspects the site) to determine if any modifications are necessary to the PSTP and/or the final prosthesis design. If a modification(s) is necessary, the PSTP is removed from the patient's mouth and physically modified (e.g., material is removed from the PSTP, material is added to the PSTP, or both). The modified PSTP is scanned in its entirety generating scan data and/or a virtual three-dimensional model of the modified PSTP. The modified PSTP is then reattached to the implant. Alternatively to removing the PSTP from the patient's mouth and modifying the PSTP outside of the patient's mouth, if the necessary modification(s) is supragingival, the physical modification(s) can be made to the PSTP without removing the PSTP from the patient's mouth and the PSTP can be scanned while still installed in the patient's mouth (e.g., only the viewable portion of the PSTP is scanned). The merged dataset and/or the merged virtual three-dimensional model are updated to include the scan data of the modified PSTP and/or the virtual three-dimensional model of the modified PSTP. The final prosthesis is then designed and fabricated as a replica of the modified PSTP (e.g., a copymill) using the updated merged dataset and/or the updated merged virtual three-dimensional model (e.g., the final prosthesis includes a titanium abutment with a porcelain coated ceramic crown). The modified PSTP is removed and the final prosthesis is attached to the implant.

According to a fifth alternative, a method of manufacturing a permanent patient-specific prosthesis (e.g., a final prosthesis) for attachment to a dental implant (e.g., implant 60) installed in a mouth of a patient includes installing a dental implant into the mouth of the patient. Then a PSTP is fabricated. The fabricated PSTP is scanned in its entirety generating scan data and/or a virtual three-dimensional model of the PSTP. Then the PSTP is attached to the implant installed in the patient's mouth. The gingival tissue is permitted to heal and then a clinician assesses the site (e.g., visually inspects the site) to determine if any modifications are necessary to the PSTP and/or the final prosthesis design. If a modification(s) is necessary, the PSTP is removed from the patient's mouth and physically modified (e.g., material is removed from the PSTP, material is added to the PSTP, or both). The modified PSTP is scanned in its entirety generating scan data and/or a virtual three-dimensional model of the modified PSTP. The modified PSTP is then reattached to the implant. The final prosthesis is then designed and fabricated as a replica of the modified PSTP (e.g., a copymill) using the scan data of the modified PSTP and/or the virtual three-dimensional model of the modified PSTP (e.g., the final prosthesis includes a titanium abutment with a porcelain coated ceramic crown). The modified PSTP is removed and the final prosthesis is attached to the implant.

According to a sixth alternative, a method of manufacturing a permanent patient-specific prosthesis (e.g., a final prosthesis) for attachment to a dental implant (e.g., implant 60) installed in a mouth of a patient includes installing a dental implant into the mouth of the patient. Then a PSTP is fabricated. The fabricated PSTP is scanned in its entirety generating scan data and/or a virtual three-dimensional model of the PSTP. Then the PSTP is attached to the implant installed in the patient's mouth. After the PSTP is attached to the implant, the mouth of the patient is scanned. Specifically, the attached PSTP and the adjacent and/or opposing teeth are scanned generating additional scan data and/or a virtual three-dimensional model of the attached PSTP and the adjacent and/or opposing teeth of the patient. The additional scan data and the scan data generated from the scan of the entire PSTP are merged into a merged dataset and/or a merged virtual three-dimensional model. The gingival tissue is permitted to heal and then a clinician assesses the site (e.g., visually inspects the site) to determine if any modifications are necessary to the PSTP and/or the final prosthesis design. If a modification(s) is necessary, the scan data and/or the virtual three-dimensional model of the PSTP is virtually modified (e.g., material is virtually removed from the virtual three-dimensional model of the PSTP, material is virtually added to the virtual three-dimensional model of the PSTP, or both). The merged dataset and/or the merged virtual three-dimensional model are updated to include the virtually modified scan data of the PSTP and/or the virtually modified virtual three-dimensional model of the PSTP. The final prosthesis is then designed and manufactured as a replica of the virtually modified virtual three-dimensional model of the PSTP using the updated merged dataset and/or the updated merged virtual three-dimensional model (e.g., the final prosthesis includes a titanium abutment with a porcelain coated ceramic crown). The PSTP is removed and the final prosthesis is attached to the implant.

According to a seventh alternative, a method of manufacturing a permanent patient-specific prosthesis (e.g., a final prosthesis) for attachment to a dental implant (e.g., implant 60) installed in a mouth of a patient includes installing a dental implant into the mouth of the patient. Then a PSTP is fabricated. The fabricated PSTP is scanned in its entirety generating scan data and/or a virtual three-dimensional model of the PSTP. Then the PSTP is attached to the implant installed in the patient's mouth. The gingival tissue is permitted to heal and then a clinician assesses the site (e.g., visually inspects the site) to determine if any modifications are necessary to the PSTP and/or the final prosthesis design. If a modification(s) is necessary, the scan data and/or the virtual three-dimensional model of the PSTP is virtually modified (e.g., material is virtually removed from the virtual three-dimensional model of the PSTP, material is virtually added to the virtual three-dimensional model of the PSTP, or both). The final prosthesis is then designed and manufactured as a replica of the virtually modified virtual three-dimensional model of the PSTP using the virtually modified scan data of the PSTP (e.g., the final prosthesis includes a titanium abutment with a porcelain coated ceramic crown). The PSTP is removed and the final prosthesis is attached to the implant.

According to an eighth alternative, a method of manufacturing a permanent patient-specific prosthesis (e.g., a final prosthesis) for attachment to a dental implant (e.g., implant 60) installed in a mouth of a patient includes installing a dental implant into the mouth of the patient. Then a PSTP is virtually designed using, for example, design software (examples of such software are described herein) to create virtual PSTP data and/or a virtual three-dimensional model of a virtual PSTP. Instructions based on the virtual PSTP data and/or the virtual three-dimensional model of the virtual PSTP are sent to a milling machine and/or a rapid-prototype machine to manufacture an actual PSTP (e.g., the PSTP 10a, 10b, and 10c, or a different PSTP). Then the actual PSTP is fabricated. Then the actual PSTP is attached to the dental implant installed in the patient's mouth. After the actual PSTP is attached to the implant, the mouth of the patient is scanned. Specifically, the attached actual PSTP and the adjacent and/or opposing teeth are scanned generating scan data and/or a virtual three-dimensional model of the attached actual PSTP and the adjacent and/or opposing teeth of the patient. The scan data and the virtual PSTP data from the virtual designing of the PSTP are merged into a merged dataset and/or a merged virtual three-dimensional model. Then the location of the dental implant installed in the mouth of the patient is determined, using, for example, software configured to analyze the merged dataset and/or the merged virtual three-dimensional model. The gingival tissue is permitted to heal and then a clinician assesses the site (e.g., visually inspects the site) to determine if any modifications are necessary to the actual PSTP and/or the final prosthesis design. If a modification(s) is necessary, the virtual PSTP data and/or the virtual three-dimensional model of the virtual PSTP is virtually modified (e.g., material is virtually removed from the virtual three-dimensional model of the virtual PSTP, material is virtually added to the virtual three-dimensional model of the virtual PSTP, or both). The merged dataset and/or the merged virtual three-dimensional model are updated to include the virtually modified virtual PSTP data of the virtual PSTP and/or the virtually modified virtual three-dimensional model of the virtual PSTP. The final prosthesis is then designed and manufactured as a replica of the virtually modified virtual three-dimensional model of the virtual PSTP using the updated merged dataset and/or the updated merged virtual three-dimensional model (e.g., the final prosthesis includes a titanium abutment with a porcelain coated ceramic crown). The actual PSTP is removed and the final prosthesis is attached to the implant.

According to a ninth alternative, a method of manufacturing a permanent patient-specific prosthesis (e.g., a final prosthesis) for attachment to a dental implant (e.g., implant 60) installed in a mouth of a patient includes installing a dental implant into the mouth of the patient. Then a PSTP is virtually designed using, for example, design software (examples of such software are described herein) to create virtual PSTP data and/or a virtual three-dimensional model of a virtual PSTP. Instructions based on the virtual PSTP data and/or the virtual three-dimensional model of the virtual PSTP are sent to a milling machine and/or a rapid-prototype machine to manufacture an actual PSTP (e.g., the PSTP 10a, 10b, and 10c, or a different PSTP). Then the actual PSTP is fabricated. Then the actual PSTP is attached to the dental implant installed in the patient's mouth. After the actual PSTP is attached to the implant, the mouth of the patient is scanned. Specifically, the attached actual PSTP and the adjacent and/or opposing teeth are scanned generating scan data and/or a virtual three-dimensional model of the attached actual PSTP and the adjacent and/or opposing teeth of the patient. The scan data and the virtual PSTP data from the virtual designing of the PSTP are merged into a merged dataset and/or a merged virtual three-dimensional model. Then the location of the dental implant installed in the mouth of the patient is determined, using, for example, software configured to analyze the merged dataset and/or the merged virtual three-dimensional model. The gingival tissue is permitted to heal and then a clinician assesses the site (e.g., visually inspects the site) to determine if any modifications are necessary to the actual PSTP and/or the final prosthesis design. Assuming that the clinician determines that no modifications are necessary, the final prosthesis is designed and manufactured as a replica of the virtual three-dimensional model of the virtual PSTP (e.g., the final prosthesis includes a titanium abutment with a porcelain coated ceramic crown). The actual PSTP is removed and the final prosthesis is attached to the implant.

Figure 7:
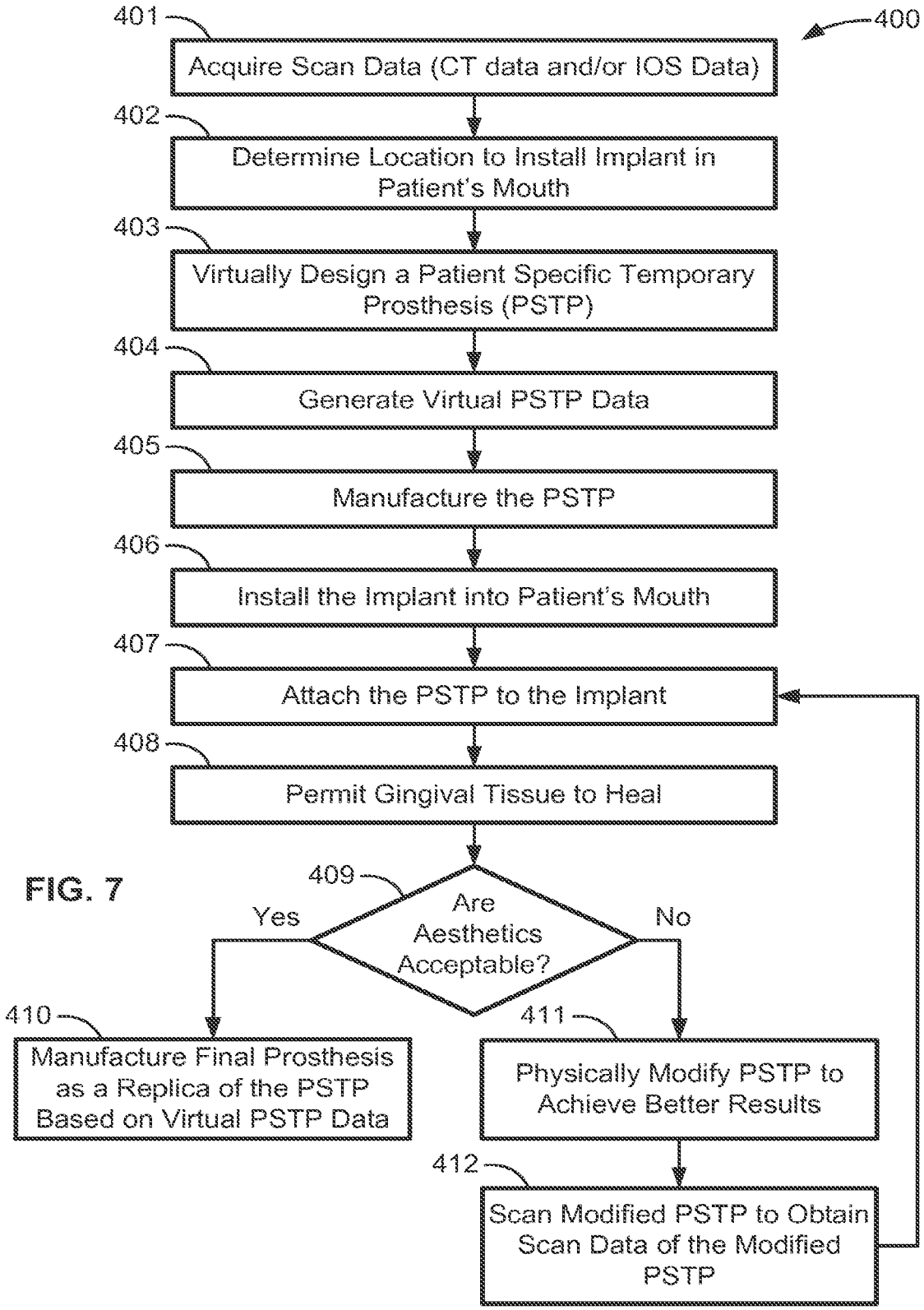

Now referring to FIG. 7, a method 400 of manufacturing a permanent patient-specific prosthesis (e.g., a final prosthesis) for attachment to a dental implant (e.g., implant 60) installed in a mouth of a patient is described in reference to a flow chart. Initially, scan data and/or virtual three-dimensional models of a patient's dental conditions are acquired (401). The scan data and/or the virtual three-dimensional models can be generated from a computed tomography (CT) scan and/or an intraoral scan (IOS) of the patient's mouth. The CT scan generates scan data representative of information regarding the bone(s) (e.g., jaw bone) and teeth in a patient's mouth and the IOS scan generates scan data representative of information regarding the soft tissues (e.g., gingival tissue) and teeth in the patient's mouth. Together, the bone, the tooth, and the tissue information can be used to develop a virtual three-dimensional model of a patient's mouth for use in planning a dental restoration site including a dental implant (e.g., implant 60) and a final prosthesis attached thereto.

Specifically, after acquiring the scan data (401), a desired location and/or orientation (e.g., pitch, yaw, and depth) to install an implant in the mouth of the patient is determined (402). The determined location can be selected or determined based on a number of different variables, such as, for example, the location, position, and orientation of the teeth adjacent to the proposed implant site, the location of where the PSTP and/or final prosthesis is proposed, the location of nerves or the sinus cavity, and/or the composition and structure of the patient's jawbone.

A PSTP is virtually designed (403) using design software to create a virtual three-dimensional model of a virtual PSTP. Examples of such software used to create a virtual three-dimensional model of a virtual PSTP include CAD Design Software available from 3Shape A/S located in Copenhagen, Denmark; DentalCAD available from exocad GmbH in Darmstadt, Germany; and DentCAD available from Delcam plc in Birmingham, United Kingdom.

Virtual PSTP data is generated (404) from the virtually designed PSTP. The virtual PSTP data can be sent as a set of instructions to a milling machine and/or a rapid-prototype machine to manufacture an actual PSTP (405). The actual PSTP can be one of the PSTPs 10a, 10b, and 10c, or a different PSTP. The actual PSTP is substantially an exact replica of the virtual three-dimensional model of the virtual PSTP designed using the design software.

The implant (e.g., implant 60) is installed into the mouth of the patient (406) at substantially the desired location as determined above (402). The implant is installed after the actual PSTP is manufactured such that the actual PSTP is ready to be installed in the patient's mouth when the implant is first installed. Alternatively, the implant can be installed prior to the actual PSTP being manufactured.

The implant can be installed using a surgical guide system for installing the dental implant at substantially the desired location in a patient's mouth. An example of such a system is the Navigator® Surgical Guide System available from Biomet 3i, LLC. Additional details on the Navigator® Surgical Guide System can be found in U.S. Patent Application Publication No. 2009/0130630, which is commonly owned by the assignee of the present application and is hereby incorporated by reference herein in its entirety.

After the implant is installed (406), the actual PSTP is attached to the implant (407). In some implementations, the PSTP is attached to the dental implant in a non-rotational fashion (e.g., using complementary non-rotational features) and held in place using a screw fastener (e.g., screw 15, 25, 35). After the PSTP is attached to the implant (407), the patient's gingival tissue is permitted to heal around the PSTP (408). The gingival tissue generally heals in a shape with an emergence contour profile that corresponds to the external contours of the PSTP abutting the gingival tissue.

After the gingival tissue is permitted to heal (408) for a predetermined amount of time (e.g., a day, two weeks, a month, three months, six months, a year, etc.), the aesthetics of the gingival tissue surrounding the PSTP are checked to determine if the aesthetics of the gingival tissue surrounding the PSTP are acceptable (409). The aesthetics check (409) is the same as the aesthetic check (106) described above in reference to the method 100.

If the aesthetics of the gingival tissue and/or of the PSTP itself are determined to be acceptable (409), a final prosthesis is manufactured as a replica of the PSTP using the virtual PSTP data (410). That is, the virtual PSTP data generated from the virtually designed PSTP (403) is used to create a physical replica of the PSTP using, for example, a milling machine and/or a rapid-prototype machine. Thus, the outer contours of the final prosthesis are the same as, or substantially the same as, the outer contours of the PSTP as both were manufactured using the same virtual PSTP data. As described above in reference to the method 100, essentially, the difference between the PSTP and the final prosthesis is the material(s) that are used to make the PSTP and the final prosthesis.

If the aesthetics are determined to not be acceptable (409), the PSTP is physically modified to achieve better results (411) and the modified PSTP is scanned to obtain scan data of the modified PSTP (412) and/or a virtual three-dimensional model of the modified PSTP. The physical modification (411) and the scanning of the modified PSTP (412) are the same as the physical modification (108) and the scanning of the modified PSTP (109) described above in reference to the method 100. After the modified PSTP is scanned (412), the PSTP is reattached to the implant (407) and acts (408), (411), and (412) are repeated until the aesthetics are found to be acceptable (409) and then the final prosthesis is manufactured (410) based on the latest scan data from a scan of the latest modified PSTP.

Figure 8:
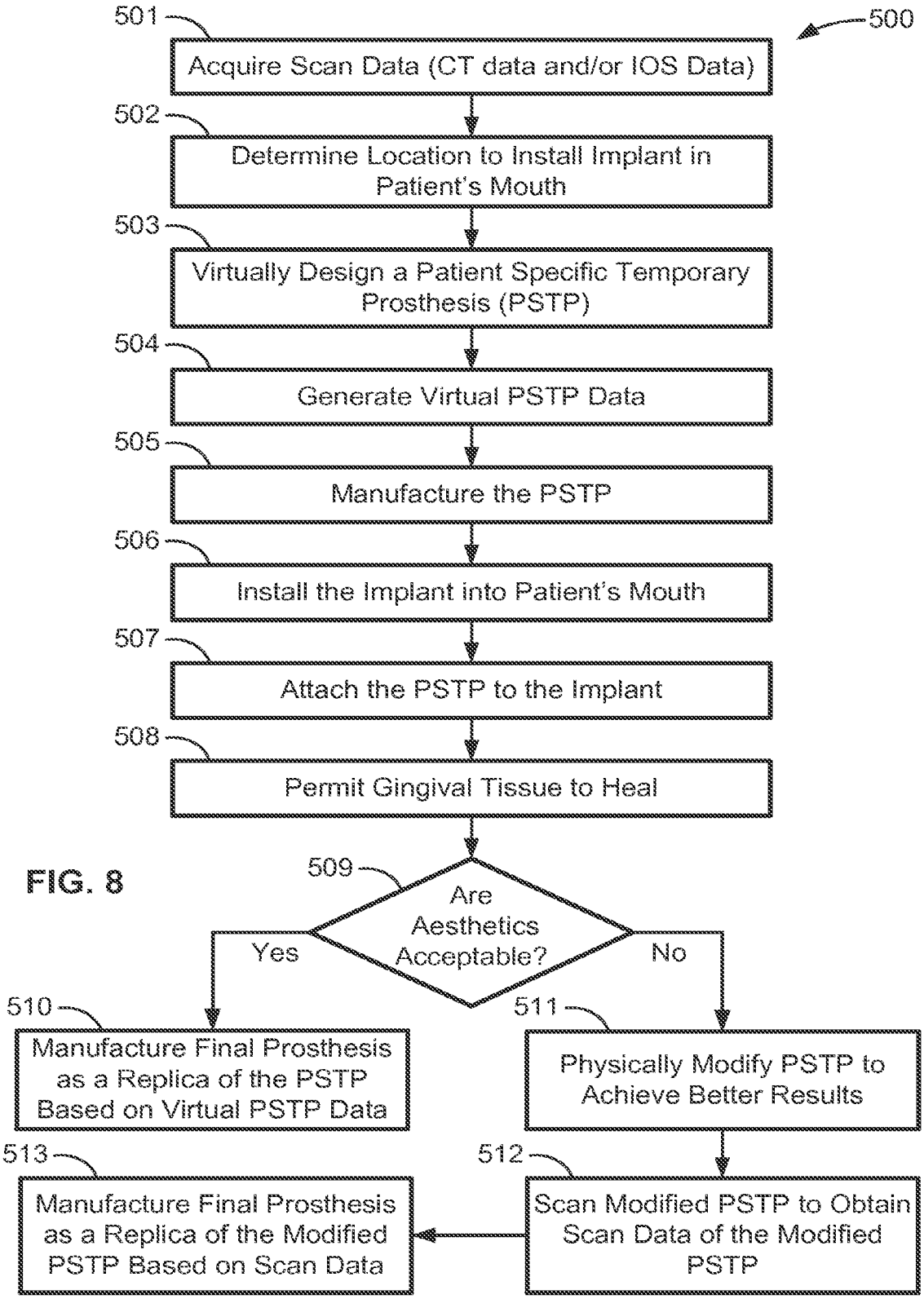

Now referring to FIG. 8, a method 500 of manufacturing a permanent patient-specific prosthesis (e.g., a final prosthesis) for attachment to a dental implant (e.g., implant 60) installed in a mouth of a patient is described in reference to a flow chart. The method 500 includes acts (501)-(512) which are the same as acts (401)-(412) described above in reference to the method 400 of FIG. 7. However, the method 500 further includes act (513) after the modified PSTP is scanned (512). After the modified PSTP is scanned (512), the final prosthesis is manufactured as a replica of the modified PSTP based on the scan data and/or the virtual three-dimensional model from the scan of the modified PSTP (512) without rechecking the aesthetics as in the method 400. That is, in the method 500, the aesthetics are not rechecked after the modifications to the PSTP (511). Foregoing the rechecking of the aesthetics in the method 500 may accelerate the treatment time for the patient as compared to the method 400. A clinician might forego the rechecking of the aesthetics when the modifications to the PSTP are minor and/or supragingival (e.g., modifications are made to the portion of the PSTP not abutting or blocked by the gingival tissue).

Figure 9:
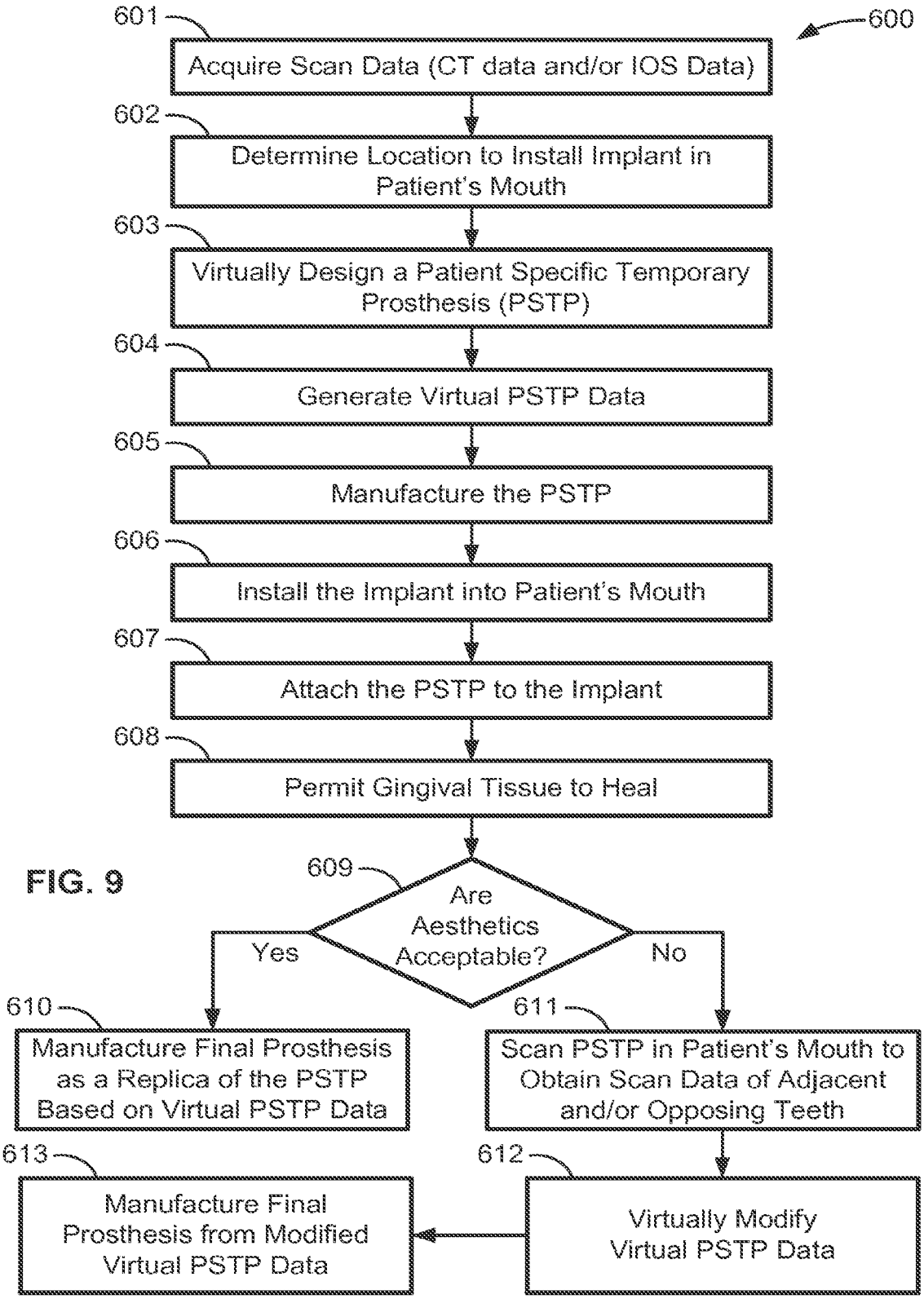

Now referring to FIG. 9, a method 600 of manufacturing a permanent patient-specific prosthesis (e.g., a final prosthesis) for attachment to a dental implant (e.g., implant 60) installed in a mouth of a patient is described in reference to a flow chart. The method 600 includes acts (601)-(610) which are the same as acts (401)-(410) described above in reference to the method 400 of FIG. 7. However, the method 600 replaces acts (411) and (412) with acts (611), (612), and (613) in response to the aesthetics being determined to not be acceptable (609).

If the aesthetics are determined to not be acceptable (609), the patient's mouth is scanned to obtain additional scan data (611) and/or a virtual three-dimensional model of at least a portion of the patient's mouth. In some implementations, the installed actual PSTP, the adjacent gingival tissue healing therearound, and adjacent and/or opposing teeth are scanned to generate scan data and/or a virtual three-dimensional model of the actual PSTP, the adjacent gingival tissue, and the adjacent and/or opposing teeth. Then, the originally generated virtual PSTP data (604) is virtually modified (612). Specifically, the virtual PSTP data and/or the virtual three-dimensional model of the virtual PSTP are virtually modified by the clinician treating the patient and/or another designer. The virtual modifications can be made to the virtual PSTP data and/or the virtual three-dimensional model of the virtual PSTP with the actual PSTP remaining in the patient's mouth (e.g., the actual PSTP does not need to be removed for the virtual modification). The virtual modifications can include virtually removing material from the virtual three-dimensional model of the virtual PSTP and/or virtually adding material to the virtual three-dimensional model of the virtual PSTP. A clinician might virtually modify the virtual PSTP data of the virtual PSTP (instead of physically modifying the actual PSTP) when the modifications to the PSTP are minor (e.g., the modifications will not significantly impact the healing of the gingival tissue) and/or supragingival (e.g., modifications are made to the portion of the PSTP not abutting or blocked by the gingival tissue).

After the virtual PSTP data and/or the virtual three-dimensional model of the virtual PSTP are virtually modified (612), the final prosthesis is manufactured as a replica of the virtually modified virtual three-dimensional model of the virtual PSTP (613). Specifically, the final prosthesis is manufactured based on the virtually modified virtual PSTP data without rechecking the aesthetics as in the method 400 and without physically modifying the actual PSTP installed in the mouth of the patient as in the method 500. That is, in the method 600, the aesthetics are not rechecked after the virtual modifications to the virtual PSTP data (612) and the PSTP installed in the mouth of the patient is not physically modified. As described above, foregoing the rechecking of the aesthetics in the method 600 may accelerate the treatment time for the patient as compared to the method 400. Additionally, foregoing the physical modification to the PSTP avoids and/or reduces potential discomfort and tissue remodeling of the patient resulting from having to endure removal of and replacement of the PSTP during such physical modifications.

Several alternative implementations which are similar to the methods 400, 500, and 600 are described below. According to a first alternative, a method of manufacturing a permanent patient-specific prosthesis (e.g., a final prosthesis) for attachment to a dental implant (e.g., implant 60) installed in a mouth of a patient includes acquiring scan data and/or virtual three-dimensional models of a patient's dental conditions (e.g., CT data and/or IOS data). Then a desired location and/or orientation of an implant in the patient's mouth are determined. A three-dimensional model of a virtual PSTP is designed. An actual PSTP is fabricated (e.g., using a milling machine and/or a rapid-prototype machine) as an actual replica of the three-dimensional model of the virtual PSTP. After the PSTP is fabricated, the implant is installed in the mouth of the patient using a surgical guide system (e.g., Navigator Surgical Guide System) and the actual PSTP is attached to the installed implant. The gingival tissue is permitted to heal and then a clinician assesses the site (e.g., visually inspects the site) to determine if any modifications are necessary to the PSTP and/or the final prosthesis design. If no modification(s) are necessary, the final prosthesis is designed and fabricated as an actual replica of the three-dimensional model of the virtual PSTP (which is also a replica of the actual PSTP). The PSTP is removed and the final prosthesis is attached to the implant.

According to a second alternative, a method of manufacturing a permanent patient-specific prosthesis (e.g., a final prosthesis) for attachment to a dental implant (e.g., implant 60) installed in a mouth of a patient includes acquiring scan data and/or virtual three-dimensional models of a patient's dental conditions (e.g., CT data and/or IOS data). Then a desired location and/or orientation of an implant in the patient's mouth are determined. A three-dimensional model of a virtual PSTP is designed. An actual PSTP is fabricated (e.g., using a milling machine and/or a rapid-prototype machine) as an actual replica of the three-dimensional model of the virtual PSTP. After the PSTP is fabricated, the implant is installed in the mouth of the patient using a surgical guide system (e.g., Navigator Surgical Guide System) and the actual PSTP is attached to the installed implant. Then the final prosthesis is designed and fabricated as an actual replica of the three-dimensional model of the virtual PSTP (which is also a replica of the actual PSTP). The gingival tissue is permitted to heal and then the PSTP is removed and the final prosthesis is attached to the implant. In such an implementation, the clinician does not assess the site (e.g., visually inspects the site) to determine if any modifications are necessary to the PSTP and/or the final prosthesis design as the final prosthesis is designed and fabricated without waiting for the gingival tissue to heal.

According to a third alternative, a method of manufacturing a permanent patient-specific prosthesis (e.g., a final prosthesis) for attachment to a dental implant (e.g., implant 60) installed in a mouth of a patient includes acquiring scan data and/or virtual three-dimensional models of a patient's dental conditions (e.g., CT data and/or IOS data). Then a desired location and/or orientation of an implant in the patient's mouth are determined. A three-dimensional model of a virtual PSTP is designed. An actual PSTP is fabricated (e.g., using a milling machine and/or a rapid-prototype machine) as an actual replica of the three-dimensional model of the virtual PSTP. After the PSTP is fabricated, the implant is installed in the mouth of the patient using a surgical guide system (e.g., Navigator Surgical Guide System) and the actual PSTP is attached to the installed implant. The gingival tissue is permitted to heal and then a clinician assesses the site (e.g., visually inspects the site) to determine if any modifications are necessary to the PSTP and/or the final prosthesis design. If modification(s) are necessary, the PSTP is removed from the patient's mouth and physically modified (e.g., material is removed from the PSTP, material is added to the PSTP, or both). The modified PSTP is scanned in its entirety generating scan data and/or a virtual three-dimensional model of the modified PSTP. The modified PSTP is then reattached to the implant. Alternatively to removing the PSTP from the patient's mouth and modifying the PSTP outside of the patient's mouth, if the necessary modification(s) is supragingival, the physical modification(s) can be made to the PSTP without removing the PSTP from the patient's mouth and the PSTP can be scanned while still installed in the patient's mouth (e.g., only the viewable portion of the PSTP is scanned). In some implementations, the scan data and/or the virtual three-dimensional models of a patient's dental conditions is updated to include the scan data and/or the virtual three-dimensional model of the modified PSTP. The final prosthesis is then designed and fabricated as a replica of the modified PSTP (e.g., a copymill) using the scan data of the modified PSTP and/or the virtual three-dimensional model of the modified PSTP. The modified PSTP is removed and the final prosthesis is attached to the implant.

According to a fourth alternative, a method of manufacturing a permanent patient-specific prosthesis (e.g., a final prosthesis) for attachment to a dental implant (e.g., implant 60) installed in a mouth of a patient includes acquiring scan data and/or virtual three-dimensional models of a patient's dental conditions (e.g., CT data and/or IOS data). Then a desired location and/or orientation of an implant in the patient's mouth are determined. A three-dimensional model of a virtual PSTP is designed. An actual PSTP is fabricated (e.g., using a milling machine and/or a rapid-prototype machine) as an actual replica of the three-dimensional model of the virtual PSTP. After the PSTP is fabricated, the implant is installed in the mouth of the patient using a surgical guide system (e.g., Navigator Surgical Guide System) and the actual PSTP is attached to the installed implant. The gingival tissue is permitted to heal and then a clinician assesses the site (e.g., visually inspects the site) to determine if any modifications are necessary to the PSTP and/or the final prosthesis design. If modification(s) are necessary, the three-dimensional model of the virtual PSTP is virtually modified (e.g., material is virtually removed from the three-dimensional model of the virtual PSTP, material is virtually added to the three-dimensional model of the virtual PSTP, or both). The scan data and/or the virtual three-dimensional models of a patient's dental conditions are updated to include the virtually modified three-dimensional model of the virtual PSTP. The final prosthesis is then designed and fabricated as a replica of the virtually modified three-dimensional model of the virtual PSTP using the updated scan data and/or the updated virtual three-dimensional models of a patient's dental conditions. The PSTP is removed and the final prosthesis is attached to the implant.

According to a fifth alternative, a method of manufacturing a permanent patient-specific prosthesis (e.g., a final prosthesis) for attachment to a dental implant (e.g., implant 60) installed in a mouth of a patient includes acquiring scan data and/or virtual three-dimensional models of a patient's dental conditions (e.g., CT data and/or IOS data). Then a desired location and/or orientation of an implant in the patient's mouth are determined. A three-dimensional model of a virtual PSTP is designed. An actual PSTP is fabricated (e.g., using a milling machine and/or a rapid-prototype machine) as an actual replica of the three-dimensional model of the virtual PSTP. After the PSTP is fabricated, the implant is installed in the mouth of the patient using a surgical guide system (e.g., Navigator Surgical Guide System) and the actual PSTP is attached to the installed implant. The gingival tissue is permitted to heal and then a clinician assesses the site (e.g., visually inspects the site) to determine if any modifications are necessary to the PSTP and/or the final prosthesis design. If modification(s) are necessary, the three-dimensional model of the virtual PSTP is virtually modified (e.g., material is virtually removed from the three-dimensional model of the virtual PSTP, material is virtually added to the three-dimensional model of the virtual PSTP, or both). The final prosthesis is then designed and fabricated as a replica of the virtually modified three-dimensional model of the virtual PSTP. The PSTP is removed and the final prosthesis is attached to the implant.

Figure 10:
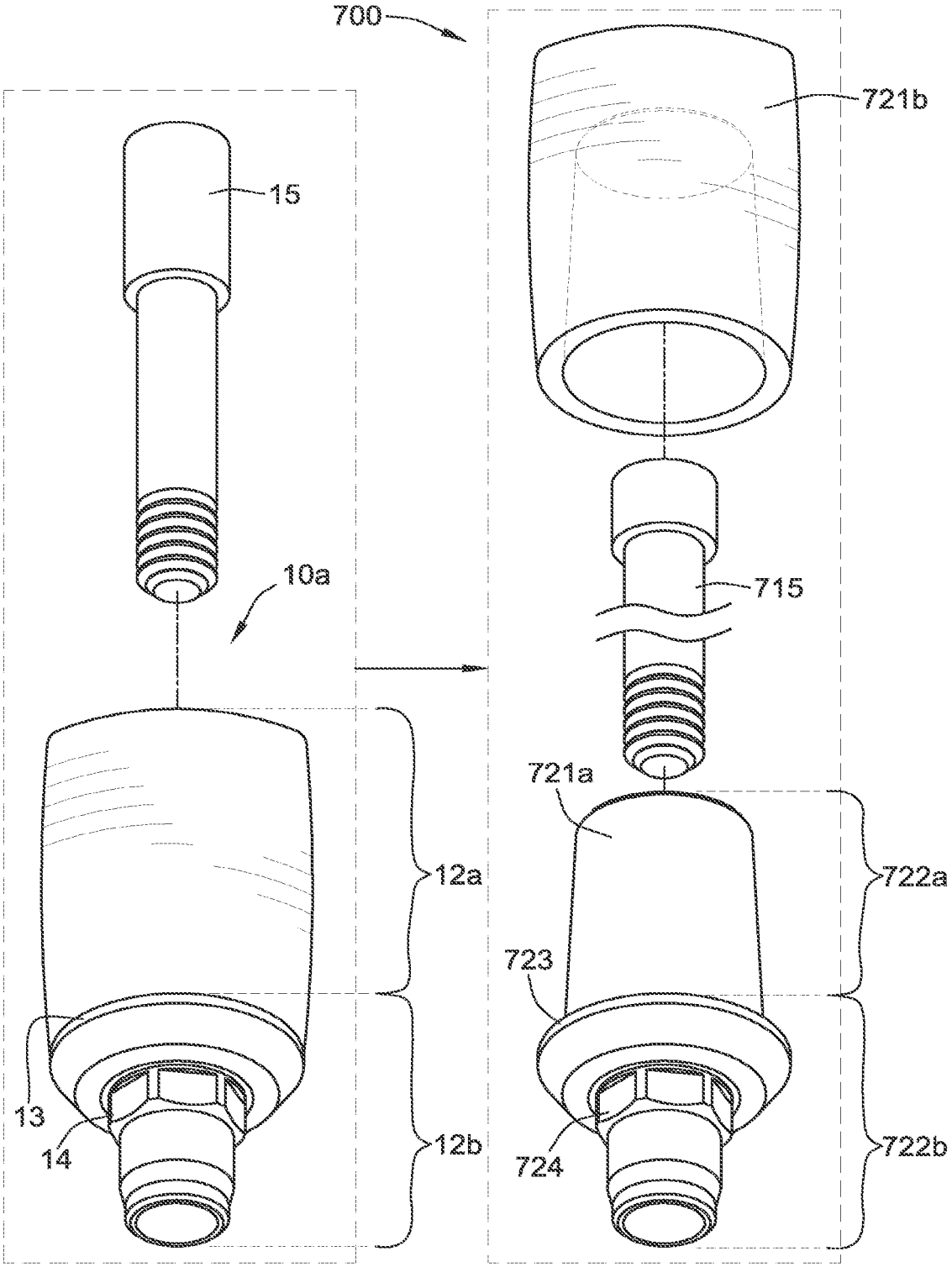
FIG. 10 is a perspective view illustrating a temporary prosthesis used to develop a permanent prosthesis*; and*
Figure 11:
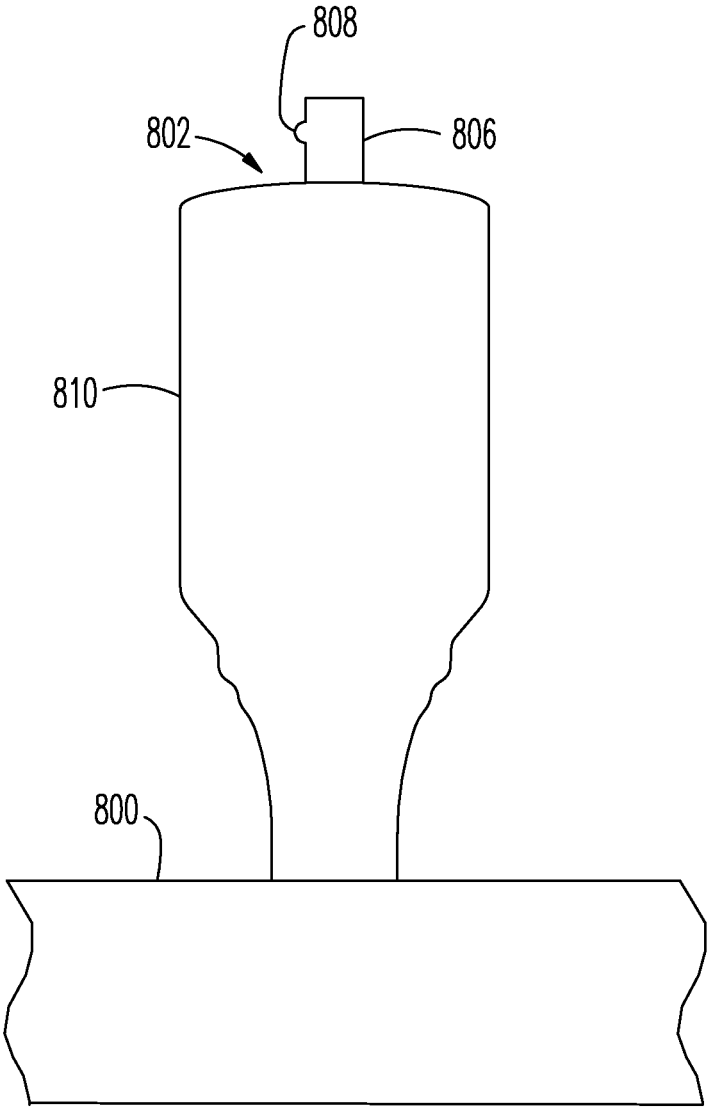
FIG. 11 is a cross-sectional view of a temporary prosthesis coupled to a scanning aid according to some aspects of the present disclosure.

Regardless of which one of the methods 100, 200, 300, 400, 500, 600 (or one of the alternative methods described herein) that is implemented, a permanent patient-specific prosthesis is manufactured to replace a PSTP. As shown in FIG. 10, the PSTP 10a is replaced with a final prosthesis 700. The final prosthesis 700 is similar to the PSTP 10b (e.g., both are two piece prostheses) in that the final prosthesis 700 includes a final or permanent abutment 721a and a final or permanent crown 721b. The permanent crown 721b is separate from the permanent abutment 721a such that a screw 725 can attach the permanent abutment 721a to the implant 60 and the permanent crown 721b can then be attached to the permanent abutment 721a thereafter using, for example, dental cement or the like.

The permanent abutment 721a has a supragingival region 722a and a subgingival region 722b, which are separated by a flange 723. The subgingival region 722b includes an anti-rotational feature 724 (the same as, or similar to, the anti-rotational feature 14) for mating with a corresponding anti-rotational feature of the implant 60. The permanent abutment 721a can be made of titanium, gold, ceramic, PEEK, acrylic, or other metals, plastics, and/or composites, or any combination thereof. The permanent crown 721b can be made of ceramic, porcelain, gold, titanium, PEEK, acrylic, or other metals, plastics, and/or composites, or any combination thereof.

While the final prosthesis 700 is shown as being a two piece solution, the final prosthesis can be made of any number of parts. For example, the final prosthesis can be one-piece made entirely of ceramic. For another example, the final prosthesis can be one piece made of ceramic with a coating of porcelain on the supragingival portion. For another example, the final prosthesis can include a titanium permanent abutment with a permanent crown attached thereto made of ceramic with a coating of porcelain thereon. Thus, while the scan data (or modified scan data) is generated from scans of monolithic PSTPs, the scan data (or modified scan data)—used to manufacture the final prostheses described herein—can be partitioned and/or modified to support fabrication of multi-piece final prostheses therefrom.

While the PSTP 10a, the temporary abutments 21a and 31a, and the permanent abutment 721a are shown and described herein as having a subgingival region, a supragingival region, and a flange therebetween, any portion of the flange and/or of the supragingival region can be placed subgingival (e.g., below the gingival tissue) for a given installation. Similarly, any portion of the flange and/or of the subgingival region can be placed supragingival (e.g., above the gingival tissue) for a given installation. Moreover, the supragingival regions described herein can be referred to as a post region that is partially subgingival and/or partially supragingival. That is, in some instances, the terms supragingival and post can be used interchangeably when referring to the various portions of the temporary abutments described herein.

As described in reference to FIG. 4, a final prosthesis is manufactured as a replica of the PSTP using the scan data generated from the scan of the PSTP to fabricate the final prosthesis. Alternatively, to the final prosthesis being an exact replica of the PSTP fabricated from the scan data of the PSTP, a portion(s) of the scan data and/or the three-dimensional model of the PSTP can be modified or replaced with stock model elements. Specifically, in such alternatives, some of the features of the PSTP represented in the scan data and/or the three-dimensional model of the PSTP correlate with stock (non-anatomic) elements such as the abutment connection, the non-rotational feature, the seating platform, and the screw access hole (e.g., generally the portion of the PSTP that interacts with the implant). The scan data and/or the three-dimensional model of the PSTP can be compared against a CAD library containing all known stock elements. A shape matching algorithm can be used to identify and replace such elements in the scan data and/or the three-dimensional model of the PSTP so that when the final prosthesis is manufactured from the scan data, the replaced features in the scan data can be manufactured using stock design parameters and not the parameters from the scan data and/or the three-dimensional model of the PSTP.

While the illustrated implementations have been primarily described with reference to the development of a permanent patient-specific prosthesis for a single tooth application, it should be understood that the present invention is also useful in multiple-tooth applications, such as bridges and bars for supporting full or partial dentures. In those situations, the permanent patient-specific prosthesis would not necessarily need a non-rotational feature for engaging the underlying implant(s) because the final prosthesis would also be supported by another structure in the mouth (e.g., one or more additional underlying implants), which would inherently achieve a non-rotational aspect to the design. In any event, using scan data generated from scanning a multiple-tooth PSTP to obtain the necessary information to fabricate a permanent multiple-tooth permanent patient-specific prosthesis can lead to the development of an aesthetically pleasing multiple-tooth system.

The above disclosure focuses on using PSTPs to develop permanent patient-specific prostheses. As discussed above, the exemplary PSTPs 10a, 10b, 10c serve as gingival healing abutments as their exterior surfaces are contoured to aid in the healing of a patient's gingival tissue. Alternatively to using a PSTP as described in any of the above implementations, a patient-specific gingival healing abutment ("PSHA") can be used instead. A PSHA is similar to a PSTP, however, a PSHA does not function as a temporary tooth. Rather a PSHA only functions to aid in healing gingival tissue therearound in an anatomical shape. Thus, the PSHA does not protrude a significant amount from a patient's gingival tissue to be used as a temporary tooth (e.g., for chewing food). A clinician might desire using a PSHA instead of a PSTP if a temporary tooth solution is not necessary for the patient, or if the design and fabrication of the PSTP would be overly complex (e.g., adjacent and/or opposing teeth are in less than ideal positions), or to reduce treatment time (e.g., it takes more time to develop and fabricate a PSTP than a PSHA). In such a solution using a PSHA, the clinician still goes through essentially the same acts as described herein to develop and fabricate the permanent patient-specific prosthesis. The main difference is that the PSTP would be replaced with a PSHA and the permanent patient-specific prosthesis would be fabricated following methods similar to those described herein. Specifically, in some implementations, the PSHA is scanned and then attached to the implant in the patient's mouth. The gingival tissue is permitted to heal and then a clinician assesses the site (e.g., visually inspects the site) to determine if any modifications are necessary to the PSHA and/or the final prosthesis design. If no modification(s) are necessary, the final prosthesis is digitally designed and fabricated using the scan data and/or the virtual three-dimensional model of the PSHA from the scan of the PSHA.

Throughout the disclosure reference is made to scanning a PSTP to generate scan data and/or a virtual three-dimensional model of the PSTP that captures all of the contours and details of the PSTP. In addition to capturing the physical contours (e.g., size, shape, dimensions, etc.), the color of the PSTP can be captured for use in designing and fabricating a permanent patient-specific prosthesis. Further, any of the scanning operations described herein can include obtaining color information. For example, scans of the installed PSTP and adjacent and/or opposing teeth can be scanned to generate scan data and/or a virtual three-dimensional model of the PSTP and the adjacent and/or opposing teeth that includes color information.

Alternatively to designing and fabricating a permanent patient-specific prosthesis as a replica of a PSTP as described herein, the permanent patient-specific prosthesis can be designed and fabricated (e.g., at least in part) using a fixture-level (e.g., implant level) model of a patient's mouth. The fixture-level model can be either a virtual model and/or a physical model (e.g., a rapid prototype model) of the patient's mouth. In the case of using a virtual fixture-level model, the permanent patient-specific prosthesis can be virtually designed (e.g., there is no need to fabricate a physical model) and in the case of using a physical fixture-level model, the permanent patient-specific prosthesis can be manually designed. The rapid prototype model of the patient's mouth can be created using a rapid prototype machine that fabricates the rapid prototype model from a fixture-level virtual three-dimensional model of the patient's mouth. To generate such a fixture-level virtual three-dimensional model of the patient's mouth, two scans are taken. First, the PSTP is scanned in its entirety to generate scan data and/or a virtual three-dimensional model of the entire PSTP. Second, the installed PSTP and adjacent and/or opposing teeth are scanned to generate scan data and/or a virtual three-dimensional model of the PSTP and the adjacent and/or opposing teeth. Then using Boolean operations (e.g., subtractive operations), the virtual three-dimensional model of the PSTP is subtracted from the virtual three-dimensional model of the PSTP and the adjacent and/or opposing teeth, which results in the fixture-level virtual three-dimensional model of the patient's mouth. Rapid prototype instructions can be generated from the fixture-level virtual three-dimensional model of the patient's mouth and sent to the rapid prototype machine to fabricate the rapid-prototype model for use in creating the permanent patient-specific prosthesis. According to some further alternatives, in the case that the PSTP is modified (physically or virtually as described above), the fixture-level virtual three-dimensional model of the patient's mouth can be updated and/or modified accordingly prior to being fabricated as the rapid prototype model used in creating the permanent patient-specific prosthesis.

According to some implementations of the disclosed concepts herein, a PSTP is scanned to obtain scan data and/or a virtual three-dimensional model of the PSTP. Such implementations are typically carried out by a clinician that has use of a scanner (e.g., a desktop scanner and/or an intraoral scanner). In some instances, the PSTP cannot be scanned directly because the clinician does not have access to an appropriate scanner. Thus, instead of scanning the PSTP as described herein, an impression is made of the PSTP. The impression can be sent to a laboratory that does have access to an appropriate scanner that can scan the impression of the PSTP to generate a virtual three-dimensional model of the PSTP therefrom. The generated virtual three-dimensional model of the PSTP from the impression is the same as, or substantially the same as, the virtual three-dimensional model of the PSTP generated from a direct scan of the PSTP described herein.

Further, a physical model (e.g., stone die cast model) of the PSTP can be created from the impression of the PSTP that can be scanned in lieu of the impression being scanned. That is, the impression can be used to create a physical model of the PSTP and the physical model of the PSTP can be scanned using an appropriate scanner (e.g., desktop and/or intraoral scanner). The scanning of the physical model of the PSTP generates scan data and/or a virtual three-dimensional model of the physical model of the PSTP, which is the same as, or substantially the same as, the virtual three-dimensional model of the PSTP generated from a direct scan of the PSTP described herein. No matter how the scan data and/or the virtual three-dimensional model of the PSTP is acquired (directly scanning the PSTP, scanning an impression of the PSTP, or scanning a physical model of the PSTP), such scan data and/or such virtual three-dimensional model of the PSTP can be used in accordance with any of the methods and implementations described throughout this disclosure.

In addition to taking an impression of the PSTP and/or creating a physical model of the PSTP, an impression of the patient's mouth with the PSTP installed therein can be taken. A physical model of the patient's mouth including the PSTP can be made from the impression. The impression and/or the physical model of the patient's mouth can then be scanned to generate scan data and/or a virtual three-dimensional model of the patient's mouth. Such a virtual three-dimensional model of the patient's mouth can be used in accordance with any of the methods and implementations described throughout this disclosure. For example, using Boolean operations (e.g., subtractive operations), the virtual three-dimensional model of the PSTP (obtained from a scan of the impression or physical model of the PSTP) can be removed from the virtual three-dimensional model of the patient's mouth (obtained from a scan of the impression or physical model of the patient's mouth) to develop a fixture level virtual three-dimensional model. In some implementations, a rapid prototype model of the developed fixture level virtual three-dimensional model can be made for use in designing and/or fabricating a permanent patient-specific prosthesis.

According to the above alternative implementations using impressions of a PSTP, a method of manufacturing a permanent patient-specific prosthesis (e.g., a final prosthesis) for attachment to a dental implant (e.g., implant 60) installed in a mouth of a patient includes installing a dental implant into the mouth of the patient. Then a PSTP is fabricated. The fabricated PSTP is entirely impressed with impression material. In some implementations, a first box is filled with impression material and approximately half of the PSTP is submerged into the material. Then, a second box is mated with the first box and impression material is then injected into the assembled boxes. The boxes are then separated, leaving a negative impression or image of two halves of the PSTP. In some implementations, the two impression halves are scanned generating scan data and/or a virtual three-dimensional model of the impressed PSTP. Such scan data and such a virtual three-dimensional model of the impressed PSTP can be processed into a virtual three-dimensional model of the PSTP. In some other implementations, a physical model of the PSTP is created using the two impression halves and the physical model is scanned in its entirety generating scan data and/or a virtual three-dimensional model of the physical model of the PSTP. After the PSTP is impressed, the PSTP is attached to the implant installed in the patient's mouth. After the PSTP is attached to the implant, the mouth of the patient can be impressed to create an impression of the patient's mouth. Specifically, the attached PSTP and the adjacent and/or opposing teeth are impressed. The impression of the patient's mouth and/or a physical model of the patient's mouth made from the impression is scanned to generate additional scan data and/or a virtual three-dimensional model of the attached PSTP and the adjacent and/or opposing teeth of the patient. The additional scan data and the scan data generated from the scan of the impression of the PSTP or from the scan of the physical model of the PSTP can be merged into a merged dataset and/or a merged virtual three-dimensional model. The gingival tissue is permitted to heal and then a clinician assesses the site (e.g., visually inspects the site) to determine if any modifications are necessary to the PSTP and/or the final prosthesis design. If a modification(s) is necessary, the PSTP is removed from the patient's mouth and physically modified (e.g., material is removed from the PSTP, material is added to the PSTP, or both). The modified PSTP can be impressed and a modified physical model of the modified PSTP can be created therefrom. The impression of the modified PSTP or the physical model of the modified PSTP is scanned in its entirety generating scan data and/or a virtual three-dimensional model representative of the modified PSTP. The modified PSTP is then reattached to the implant. Alternatively to removing the PSTP from the patient's mouth and modifying the PSTP outside of the patient's mouth, if the necessary modification(s) is supragingival, the physical modification(s) can be made to the PSTP without removing the PSTP from the patient's mouth and the PSTP can be impressed while still installed in the patient's mouth (e.g., only the viewable portion of the PSTP is impressed). The merged dataset and/or the merged virtual three-dimensional model can be updated to include the scan data representative of the modified PSTP and/or the virtual three-dimensional model representative of the modified PSTP. The final prosthesis is then designed and fabricated as a replica of the modified PSTP (e.g., a copymill) using the updated merged dataset and/or the updated merged virtual three-dimensional model. The modified PSTP is removed and the final prosthesis is attached to the implant. In the above alternative implementation, the impressions can be taken at a first location (e.g., clinician's office) and the scanning of the impressions and/or physical models can occur at a second remote location (e.g., laboratory). In addition to creating the physical model of the patient's mouth described above, a fixture-level rapid prototype model of the patient's mouth can be created from the obtained scan data for use in designing and/or fabricating the final prosthesis.

Throughout the present disclosure reference is made to scanning a PSTP to generate scan data and/or a virtual three-dimensional model of the PSTP that captures all of the contours and details of the PSTP. According to some implementations of the disclosed concepts herein, the scanning of the PSTP includes positioning the PSTP within and/or attaching the PSTP to a fixture (not shown). The fixture can be, for example, a base (e.g., a block of material) that includes a non-rotational feature (e.g., a hexagonal boss, etc.) with a central axis, where the non-rotational feature is configured to mate with a corresponding non-rotational feature (e.g., a hexagonal socket, etc.) of the PSTP. Thus, attachment of the PSTP to the fixture automatically orients the PSTP (1) such that the non-rotational feature of the PSTP corresponds with the orientation of the non-rotational feature of the fixture; (2) such that a central axis of the PSTP corresponds with (e.g., is coincident with) the central axis of the non-rotational feature of the fixture; and (3) such that a seating surface of the PSTP corresponds with a top surface feature of the fixture. The fixture (and its non-rotational feature) is positioned at a known location (e.g., position and orientation) with respect to the scanner used to scan the PSTP. Thus, attachment of the PSTP to the fixture automatically provides the scanner (and/or scanning software) with (1) the orientation of the non-rotational feature of the PSTP; (2) the location of the central axis of the PSTP; (3) the location of the seating surface of the PSTP; and (4) the location of the screw access hole of the PSTP. As such, the accuracy of the scan (e.g., the acquisition of the scan data associated with the PSTP) of the PSTP can be improved by reducing the amount of scan data (e.g., image data) that needs to be stitched together to develop the virtual three-dimensional model of the PSTP. For example, knowledge of the orientation of the non-rotational feature of the PSTP permits the scanning software to automatically include interface geometry (e.g., the non-rotational feature) of the PSTP (e.g., using stock data associated with known PSTP interfaces that mate with the fixture). That is, the portion of the scan data associated with the non-rotational feature of the PSTP is not needed and can be replaced with stock known data that is stitched with the rest of the scan data. Similarly, for another example, knowledge of the central axis of the PSTP permits the scanning software to automatically include a screw access hole of the PSTP (e.g., a bore for receiving the screw therethrough to attach the PSTP to the dental implant) in the same, or similar, manner described above in reference to the interface geometry.

Throughout the present disclosure reference is made to scanning a PSTP to generate scan data and/or a virtual three-dimensional model of the PSTP that captures all of the contours and details of the PSTP. According to some implementations of the disclosed concepts herein, the scanning of the PSTP 810 includes temporarily attaching a scanning aid 800 to the PSTP 810 prior to scanning the PSTP 810. The scanning aid 800 is designed to be coupled with the screw access hole 802 of the PSTP 810 (e.g., the bore for receiving the screw therethrough to attach the PSTP to the dental implant) and to extend therefrom such that a portion of the scanning aid protrudes from the PSTP 810 and is visible relative to the PSTP 810. The scanning aid 800 can include a first portion for engaging with the screw access hole 802 of the PSTP *810* (e.g., in a press-fit type slideable engagement) and a protrusion 806 for protruding from the screw access hole 802 of the PSTP [810,] *810*. The protrusion 806 includes a known feature 808 (e.g., a marking, a dot, a divot, a pimple, a dimple, a character, a line, a notch, etc.) on an external surface thereof that can be identified by the scanning software and used to magnify the details of the screw access hole 802 (e.g., the diameter of the screw access hole, the length of the screw access hole, etc), which are difficult to obtain by directly scanning the screw access hole 802 of the PSTP. By magnify the details, it is meant that knowledge of the orientation of the scanning aid (specifically, the protrusion and known feature thereon) relative to the rest of the scanned PSTP permits the scanning software to automatically include the screw access hole of the PSTP (e.g., using stock data associated with known PSTP screw access holes). That is, the portion of the scan data associated with the screw access hole of the PSTP is not needed and can be replaced with stock known data that is stitched with the scan data.

Further, according to some implementations of the disclosed concepts herein, the scanning of the PSTP includes temporarily attaching a scanning aid (not shown) to an implant connection and/or seating surface of the PSTP prior to scanning the PSTP. In particular, the scanning aid is designed to be coupled with the implant connection (e.g., external hexagonal boss) and to abut the seating surface of the PSTP. As such, the scanning aid extends from the seating surface of the PSTP such that the scanning aid is visible relative to the PSTP. The scanning aid can include a first portion for engaging with the implant connection of the PSTP (e.g., in a press-fit type slideable engagement where the scanning aid slides over the implant connection of the PSTP) and a second portion for extending from the implant connection of the PSTP. The second portion (and/or the first portion) includes a known feature (e.g., a marking, a dot, a divot, a pimple, a dimple, a character, a line, a notch, etc.) on an external surface thereof that can be identified by the scanning software and used to magnify the details of the implant connection and/or the seating surface (e.g., the type of implant connection, the size/diameter of the implant connection, the length/height of the implant connection, etc.), which are difficult to obtain by directly scanning the implant connection and/or the seating surface of the PSTP. By magnify the details, it is meant that knowledge of the orientation of the scanning aid (specifically, the second portion and known feature thereon) relative to the rest of the scanned PSTP permits the scanning software to automatically include the implant connection and/or seating surface of the PSTP (e.g., using stock data associated with known PSTP implant connections and/or seating surfaces). That is, the portion of the scan data associated with the implant connection and/or seating surface of the PSTP is not needed and can be replaced with stock known data that is stitched with the scan data. Further, once the knowledge of the orientation of the scanning aid permits the scanning software to automatically include the implant connection and/or seating surface of the PSTP, the screw access hole of the PSTP can also be determined and automatically included. That is, the portion of the scan data associated with the screw access hole of the PSTP is not needed and can be replaced with stock known data that is stitched with the scan data.

While the present disclosure has been described with reference to one or more particular embodiments and implementations, those skilled in the art will recognize that many changes may be made thereto without departing from the spirit and scope of the present disclosure. Each of these embodiments and implementations and obvious variations thereof is contemplated as falling within the spirit and scope of the present invention, which is set forth in the claims that follow.

What is claimed is:

1. A method of manufacturing a permanent prosthesis for attachment to a dental implant installed in a mouth of a patient, the method comprising:

fabricating a patient specific temporary prosthesis (PSTP), a supragingival portion of the PSTP having a customized anatomical tooth shape;

scanning, outside of the mouth of the patient, the PSTP to obtain scan data;

attaching the PSTP to the dental implant in the mouth of the patient;

permitting gingival tissue surrounding the PSTP to heal in the mouth of the patient for a healing time period; and in response to [gingival healing] *the gingival tissue surrounding the PSTP healing* during the healing time period:

physically modifying the PSTP by (i) removing material from the PSTP, (ii) adding material to the PSTP, or (iii) both to form a physically modified PSTP;

scanning the physically modified PSTP to obtain modified scan data; and manufacturing the permanent prosthesis using the obtained modified scan data such that all outer contours of the permanent prosthesis replicate all outer contours of the physically modified PSTP.

2. The method of claim 1, further comprising, prior to the scanning, *outside of the mouth of the patient, the PSTP to obtain scan data*, attaching a scanning aid to an implant connection of the PSTP, the scanning aid including a portion with a known feature for use in identifying the location of the implant connection of the PSTP.

3. A method of manufacturing a permanent prosthesis for attachment to a dental implant installed in a mouth of a patient, the method comprising:

fabricating a patient specific temporary prosthesis (PSTP), a supragingival portion of the PSTP having a customized anatomical tooth shape;

generating scan data from a scan of the PSTP outside the mouth of the patient; [and]

subsequent to the PSTP being attached to the dental implant *installed* in the mouth of the patient and gingival tissue surrounding the PSTP being permitted to heal in the mouth of the patient for a healing time period, generating modified scan data from a scan of a physically modified [PSTP, the PSTP being physically modified] *PSTP formed by physically modifying the PSTP* in response to gingival healing during the healing time period; and manufacturing the permanent prosthesis, based on the physically modified PSTP such that all outer contours of the permanent prosthesis replicate all outer contours of the physically modified PSTP.

4. The method of claim 3, further comprising transmitting the generated modified scan data to a milling machine and manufacturing the permanent prosthesis using the [transferred] *transmitted* modified scan data such that all outer contours of the permanent prosthesis replicate all outer contours of the physically modified PSTP.

5. The method of claim 1, further comprising removing the PSTP from the mouth of the patient.

6. The method of claim 5, wherein the physically modifying occurs prior to the PSTP being removed from the mouth of the patient, after the PSTP is removed from the mouth of the patient, or both.

*7. A method of manufacturing a permanent prosthesis for attachment to a dental implant installed in a mouth of a patient, the method comprising:*

*fabricating a patient specific temporary prosthesis (PSTP), a supragingival portion of the PSTP having a customized anatomical tooth shape;*

*subsequent to generating scan data from a scan of the PSTP outside the mouth of the patient, processing the generated scan data;*

*subsequent to the PSTP being attached to the dental implant installed in the mouth of the patient and gingival tissue surrounding the PSTP being permitted to heal in the mouth of the patient for a healing time period and generating modified scan data from a scan of a physically modified PSTP formed by physically modifying the PSTP in response to gingival healing during the healing time period, processing the modified scan data; and*

*manufacturing the permanent prosthesis based on the physically modified PSTP in the modified scan data such that all outer contours of the permanent prosthesis replicate all outer contours of the physically modified PSTP.*

* * * * *